(12) United States Patent
Lu et al.

(10) Patent No.: US 9,687,548 B2
(45) Date of Patent: Jun. 27, 2017

(54) PHOTOACTIVATABLE CAGED TAMOXIFEN AND TAMOXIFEN DERIVATIVE MOLECULES AND METHODS OF USE THEREOF

(71) Applicants: Dana-Farber Cancer Institute, Inc., Boston, MA (US); The General Hospital Corporation, Boston, MA (US)

(72) Inventors: Xin Lu, Houston, TX (US); Sarit S. Agasti, Cambridge, MA (US); Ronald A. DePinho, Houston, TX (US); Ralph Weissleder, Peabody, MA (US)

(73) Assignees: Dana-Farber Cancer Institute, Inc., Boston, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 14/395,210

(22) PCT Filed: Mar. 14, 2013

(86) PCT No.: PCT/US2013/031165
§ 371 (c)(1),
(2) Date: Oct. 17, 2014

(87) PCT Pub. No.: WO2013/158268
PCT Pub. Date: Oct. 24, 2013

(65) Prior Publication Data
US 2015/0093365 A1    Apr. 2, 2015

Related U.S. Application Data

(60) Provisional application No. 61/635,068, filed on Apr. 18, 2012.

(51) Int. Cl.
| | | |
|---|---|---|
| *A61K 41/00* | (2006.01) | |
| *A61K 31/137* | (2006.01) | |
| *A61K 31/155* | (2006.01) | |
| *A61K 31/40* | (2006.01) | |
| *A61K 31/4453* | (2006.01) | |
| *A61K 31/495* | (2006.01) | |
| *A61K 31/5375* | (2006.01) | |
| *A61K 35/12* | (2015.01) | |
| *C12N 9/00* | (2006.01) | |
| *A61K 35/30* | (2015.01) | |
| *A61K 35/32* | (2015.01) | |
| *A61K 35/34* | (2015.01) | |
| *A61K 35/35* | (2015.01) | |
| *A61K 35/36* | (2015.01) | |
| *A61K 35/44* | (2015.01) | |
| *A61K 45/06* | (2006.01) | |
| *A61K 47/48* | (2006.01) | |
| *A61N 5/06* | (2006.01) | |
| *C07C 279/08* | (2006.01) | |
| *C07C 217/18* | (2006.01) | |
| *C07D 295/088* | (2006.01) | |

(52) U.S. Cl.
CPC ........ *A61K 41/0057* (2013.01); *A61K 31/137* (2013.01); *A61K 31/155* (2013.01); *A61K 31/40* (2013.01); *A61K 31/4453* (2013.01); *A61K 31/495* (2013.01); *A61K 31/5375* (2013.01); *A61K 35/30* (2013.01); *A61K 35/32* (2013.01); *A61K 35/34* (2013.01); *A61K 35/35* (2013.01); *A61K 35/36* (2013.01); *A61K 35/44* (2013.01); *A61K 45/06* (2013.01); *A61K 47/48023* (2013.01); *A61N 5/062* (2013.01); *C07C 217/18* (2013.01); *C07C 279/08* (2013.01); *C07D 295/088* (2013.01); *C12N 9/00* (2013.01); *C07C 2101/14* (2013.01); *C07K 2319/09* (2013.01)

(58) Field of Classification Search
CPC .... A61K 31/137; A61K 31/155; A61K 31/40; A61K 31/4453; A61K 31/495; A61K 31/5375; A61K 35/30; A61K 35/32; A61K 35/34; A61K 35/35; A61K 35/36; A61K 35/44; A61K 41/0057; A61K 45/06; A61K 47/04
USPC ................. 424/93.21; 435/173.1; 514/239.2, 514/252.12, 331, 427, 428, 634, 648; 544/167, 398; 546/232
See application file for complete search history.

(56) References Cited

U.S. PATENT DOCUMENTS

| | | |
|---|---|---|
| 4,522,811 A | 6/1985 | Eppstein et al. |
| 7,883,846 B2 | 2/2011 | Miesenbock et al. |
| 2008/0120731 A1 | 5/2008 | De Strooper et al. |
| 2009/0293139 A1 | 11/2009 | Chang et al. |

OTHER PUBLICATIONS

Sinha et al. (ChemBioChem (2010), 11(5), 653-663).*
Andersson et al., "Tamoxifen administration routes and dosage for inducible Cre-mediated gene disruption in mouse hearts," *Transgenic Res.* 19(4):715-725, 2010.
(Continued)

*Primary Examiner* — Janet Epps-Smith
(74) *Attorney, Agent, or Firm* — Fish & Richardson P.C.

(57) ABSTRACT

Provided herein are compositions containing photoactivatable caged tamoxifen and tamoxifen derivative molecules. Also provided are kits containing one of these compositions and a light source. Also provided are methods of optically inducing nuclear translocation of a fusion protein containing a mammalian estrogen receptor ligand binding domain in a eukaryotic cell and methods of optically inducing recombination in a eukaryotic cell that include contacting a eukaryotic cell with at least one of these compositions. Also provided are methods of treating breast cancer in a subject that include administering a photoactivatable caged tamoxifen or tamoxifen derivative molecule to a subject having breast cancer.

17 Claims, 9 Drawing Sheets

(56) References Cited

OTHER PUBLICATIONS

Dworniczak et al., "Inducible Cre/loxP recombination in the mouse proximal tubule," *Nephron Exp. Nephrol.* 106(1):e11-e20, 2007.
Dyer et al., *J. Org. Chem.* 64:7988-7995, 1999.
El Marjou et al., "Tissue-specific and inducible Cre-mediated recombination in the gut epithelium," *Genesis* 39(3):186-193, 2004.
Fuhrmann-Benzakein et al., "Inducible and irreversible control of gene expression using a single transgene," *Nucleic Acids Res.* 28(23):E99, 2000.
Hayashi et al., "Efficient recombination in diverse tissues by a tamoxifen-inducible form of Cre: a tool for temporally regulated gene activation/inactivation in the mouse," *Dev. Biol.* 244(2):305-318, 2002.
Indra et al., "Temporally-controlled site-specific mutagenesis in the basal layer of the epidermis: comparison of the recombinase activity of the tamoxifen-inducible Cre-ER(T) and Cre-ER(T2) recombinases," *Nucleic Acids Res.* 27(22):4324-4327, 1999.
Jaskelioff et al., "Telomerase reactivation reverses tissue degeneration in aged telomerase-deficient mice," *Nature* 469(7328):102-106, 2011.
Kelly et al., "Targeted nanoparticles for imaging incipient pancreatic ductal adenocarcinoma," *PLoS Med.* 5(4):e85, 2008.
Khan et al., "Potential utility of natural products as regulators of breast cancer-associated aromatase promoters," *Reprod. Biol. Endocrinol.* 9:91, 2011.
Maeda et al., "Partial rescue of postnatal growth plate abnormalities in Ihh mutants by expression of a constitutively active PTH/PTHrP receptor," *Bone* 46(2):472-478.
Metzger et al., "Conditional site-specific recombination in mammalian cells using a ligand-dependent chimeric Cre recombinase," *Proc. Natl. Acad. Sci. U.S.A.* 92(15):6991-6995, 1995.
Muzumdar et al., "A global double-fluorescent Cre reporter mouse," *Genesis* 45(9):593-605, 2007.
Nagy, "Cre recombinase: the universal reagent for genome tailoring," *Genesis* 26(2):99, 2000.
Nair et al., "Conformational dynamics of estrogen receptors alpha and beta as revealed by intrinsic tryptophan fluorescence and circular dichroism," *J. Mol. Endocrinol.* 35(2):211-223, 2005.
Pfannkuche et al., "A Cre-based double fluorescence indicator system for monitoring cell fusion events and selection of fused cells," *Biotechniques* 48(2):113-120, 2010.
Qin et al., "Systematic comparison of constitutive promoters and the doxycycline-inducible promoter," *PLoS One* 5(5):e10611, 2010.
Sharpless et al., "Impaired nonhomologous end-joining provokes soft tissue sarcomas harboring chromosomal translocations, amplifications, and deletions," *Mol. Cell* 8(6):1187-1196, 2001.
Soriano et al., "Generalized lacZ expression with the ROSA26 Cre reporter strain," *Nat. Genetics* 21(1):70-71, 1999.
Thurber et al., "Multicolor fluorescent intravital live microscopy (FILM) for surgical tumor resection in a mouse xenograft model," *PLoS One* 4(11):e8053, 2009.
Tiede et al., "A novel mouse model for non-invasive single marker tracking of mammary stem cells in vivo reveals stem cell dynamics throughout pregnancy," *PLoS One* 4(11):e8035, 2009.
Tomita et al., "Conditional disruption of the aryl hydrocarbon receptor nuclear translocator (Arnt) gene leads to loss of target gene induction by the aryl hydrocarbon receptor and hypoxia-inducible factor 1alpha," *Mol. Endocrinol.* 14(10):1674-1681, 2000.
Tumurbaatar et al., "Cre-estrogen receptor-mediated hepatitis C virus structural protein expression in mice," *J. Virol. Methods* 146(1-2):5-13, 2007.
Vallier et al., "An efficient system for conditional gene expression in embryonic stem cells and in their in vitro and in vivo differentiated derivatives," *Proc. Natl. Acad. Sci. U.S.A.* 98(5):2467-2472.
Vandermeulen et al., "Skin-specific promoters for genetic immunisation by DNA electroporation," *Vaccine* 27(32):4272-4277, 2009.
Ventura et al., "Restoration of p53 function leads to tumour regression in vivo," *Nature* 445(7128):661-665, 2007.
Weber et al., "Temporally controlled site-specific mutagenesis in the germ cell lineage of the mouse testis," *Biol. Reprod.* 68(2):553-539, 2003.
Xue et al., "Generation of a transgenic mouse for colorectal cancer research with intestinal cre expression limited to the large intestine," *Mol. Cancer Res.* 8(8):1095, 2010.
Young et al., "Photochemical control of biological processes," *Org. Biomol. Chem.* 5(7):999, 2007.
Zinha et al., "Photoactivation of the CreER T2 recombinase for conditional site-specific recombination with high spatiotemporal resolution," *Zebrafish* 7(2):199, 2010.
Ouyang et al., "Synthetic strategies for studying embryonic development," *Chem Biol.* 17(6):590-606, 2010.
Sinha et al., "Photocontrol of Protein Activity in Cultured Cells and Zebrafish with One- and Two-Photon Illumination," *ChemBioChem* 11:653-663, 2010.
Picard, "Regulation of protein function through expression of chimaeric proteins," Current Opinion in Biotechnology 5:511-515, 1994.
International Search Report for PCT/US2013/031165 mailed Jul. 25, 2013.
Written Opinion of the International Searching Authority for PCT/US2013/031165 mailed Jul. 25, 2013.

* cited by examiner

SEQUENCE LISTING

<160> NUMBER OF SEQ ID NOS: 6

<210> SEQ ID NO 1
<211> LENGTH: 595
<212> TYPE: PRT
<213> ORGANISM: Homo sapiens

<400> SEQUENCE: 1

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

```
Pro Pro Pro Gln Leu Ser Pro Phe Leu Gln Pro His Gly Gln Gln Val
            115                 120                 125
Pro Tyr Tyr Leu Glu Asn Glu Pro Ser Gly Tyr Thr Val Arg Glu Ala
130                 135                 140
Gly Pro Pro Ala Phe Tyr Arg Pro Asn Ser Asp Asn Arg Arg Gln Gly
145                 150                 155                 160
Gly Arg Glu Arg Leu Ala Ser Thr Asn Asp Lys Gly Ser Met Ala Met
                165                 170                 175
Glu Ser Ala Lys Glu Thr Arg Tyr Cys Ala Val Cys Asn Asp Tyr Ala
            180                 185                 190
Ser Gly Tyr His Tyr Gly Val Trp Ser Cys Glu Gly Cys Lys Ala Phe
        195                 200                 205
Phe Lys Arg Ser Ile Gln Gly His Asn Asp Tyr Met Cys Pro Ala Thr
    210                 215                 220
Asn Gln Cys Thr Ile Asp Lys Asn Arg Arg Lys Ser Cys Gln Ala Cys
225                 230                 235                 240
Arg Leu Arg Lys Cys Tyr Glu Val Gly Met Met Lys Gly Gly Ile Arg
                245                 250                 255
Lys Asp Arg Arg Gly Gly Arg Met Leu Lys His Lys Arg Gln Arg Asp
            260                 265                 270
Asp Gly Glu Gly Arg Gly Glu Val Gly Ser Ala Gly Asp Met Arg Ala
        275                 280                 285
Ala Asn Leu Trp Pro Ser Pro Leu Met Ile Lys Arg Ser Lys Lys Asn
    290                 295                 300
Ser Leu Ala Leu Ser Leu Thr Ala Asp Gln Met Val Ser Ala Leu Leu
305                 310                 315                 320
Asp Ala Glu Pro Pro Ile Leu Tyr Ser Glu Tyr Asp Pro Thr Arg Pro
                325                 330                 335
Phe Ser Glu Ala Ser Met Met Gly Leu Leu Thr Asn Leu Ala Asp Arg
            340                 345                 350
Glu Leu Val His Met Ile Asn Trp Ala Lys Arg Val Pro Gly Phe Val
        355                 360                 365
Asp Leu Thr Leu His Asp Gln Val His Leu Leu Glu Cys Ala Trp Leu
    370                 375                 380
Glu Ile Leu Met Ile Gly Leu Val Trp Arg Ser Met Glu His Pro Gly
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
            420                 425                 430
Ser Arg Phe Arg Met Met Asn Leu Gln Gly Glu Glu Phe Val Cys Leu
        435                 440                 445
Lys Ser Ile Ile Leu Leu Asn Ser Gly Val Tyr Thr Phe Leu Ser Ser
    450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
            500                 505                 510
His Ile Arg His Met Ser Asn Lys Gly Met Glu His Leu Tyr Ser Met
        515                 520                 525
```

| | | | | | | | | | | | | | | |
|---|---|---|---|---|---|---|---|---|---|---|---|---|---|---|
| Lys | Cys | Lys | Asn | Val | Val | Pro | Leu | Tyr | Asp | Leu | Leu | Leu | Glu | Met | Leu |
| | 530 | | | | 535 | | | | 540 | | | | | | |

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
            565                 570                 575

His Ser Leu Gln Lys Tyr Tyr Ile Thr Gly Glu Ala Glu Gly Phe Pro
        580                 585                 590

Ala Thr Val
    595

<210> SEQ ID NO 2
<211> LENGTH: 6330
<212> TYPE: DNA
<213> ORGANISM: Homo sapiens

<400> SEQUENCE: 2

```
aggagctggc ggagggcgtt cgtcctggga ctgcacttgc tcccgtcggg tcgcccggct      60
tcaccggacc cgcaggctcc cggggcaggg ccggggccag agctcgcgtg tcggcgggac     120
atgcgctgcg tcgcctctaa cctcgggctg tgctcttttt ccaggtggcc cgccggtttc     180
tgagccttct gccctgcggg gacacggtct gcaccctgcc cgcggccacg gaccatgacc     240
atgaccctcc acaccaaagc atctgggatg gccctactgc atcagatcca agggaacgag     300
ctggagcccc tgaaccgtcc gcagctcaag atcccctgg agcggcccct gggcgaggtg     360
tacctggaca gcagcaagcc cgccgtgtac aactaccccg agggcgccgc ctacgagttc     420
aacgccgcgg ccgccgccaa cgcgcaggtc tacggtcaga ccggcctccc ctacggcccc     480
gggtctgagg ctgcggcgtt cggctccaac ggcctggggg gtttcccccc actcaacagc     540
gtgtctccga gcccgctgat gctactgcac ccgccgccgc agctgtcgcc tttcctgcag     600
ccccacggcc agcaggtgcc ctactacctg gagaacgagc ccagcggcta cacggtgcgc     660
gaggccggcc cgccggcatt ctacaggcca aattcagata tcgacgcca gggtggcaga     720
gaaagattgg ccagtaccaa tgacaaggga agtatggcta tggaatctgc caaggagact     780
cgctactgtg cagtgtgcaa tgactatgct tcaggctacc attatggagt ctggtcctgt     840
gagggctgca aggccttctt caagagaagt attcaaggac ataacgacta tatgtgtcca     900
gccaccaacc agtgcaccat tgataaaaac aggaggaaga gctgccaggc ctgccggctc     960
cgcaaatgct acgaagtggg aatgatgaaa ggtgggatac gaaaagaccg aagaggaggg    1020
agaatgttga acacaagcg ccagagagat gatgggagg gcaggggtga agtggggtct    1080
gctggagaca tgagagctgc caaccttttgg ccaagcccgc tcatgatcaa cgctctaag    1140
aagaacagcc tggccttgtc cctgacggcc gaccagatgg tcagtgcctt gttggatgct    1200
gagcccccca tactctattc cgagtatgat cctaccagac ccttcagtga agcttcgatg    1260
atgggcttac tgaccaacct ggcagacagg gagctggttc acatgatcaa ctgggcgaag    1320
agggtgccag gctttgtgga tttgaccctc catgatcagg tccaccttct agaatgtgcc    1380
tggctagaga tcctgatgat tggtctcgtc tggcgctcca tggagcaccc agggaagcta    1440
ctgtttgctc ctaacttgct cttggacagg aaccaggaa aatgtgtaga gggcatggtg    1500
gagatcttcg acatgctgct ggctacatca tctcggttcc gcatgatgaa tctgcaggga    1560
gaggagtttg tgtgcctcaa atctattatt ttgcttaatt ctggagtgta cacatttctg    1620
tccagcaccc tgaagtctct ggaagagaag gaccatatcc accgagtcct ggacaagatc    1680
```

```
acagacactt tgatccacct gatggccaag gcaggcctga ccctgcagca gcagcaccag    1740
cggctggccc agctcctcct catcctctcc cacatcaggc acatgagtaa caaaggcatg    1800
gagcatctgt acagcatgaa gtgcaagaac gtggtgcccc tctatgacct gctgctggag    1860
atgctggacg cccaccgcct acatgcgccc actagccgtg gaggggcatc cgtggaggag    1920
acggaccaaa gccacttggc cactgcgggc tctacttcat cgcattcctt gcaaaagtat    1980
tacatcacgg gggaggcaga gggtttccct gccacggtct gagagctccc tggctcccac    2040
acggttcaga taatccctgc tgcattttac cctcatcatg caccacttta gccaaattct    2100
gtctcctgca tacactccgg catgcatcca acaccaatgg ctttctagat gagtggccat    2160
tcatttgctt gctcagttct tagtggcaca tcttctgtct tctgttggga acagccaaag    2220
ggattccaag gctaaatctt tgtaacagct ctctttcccc cttgctatgt tactaagcgt    2280
gaggattccc gtagctcttc acagctgaac tcagtctatg ggttggggct cagataactc    2340
tgtgcattta agctacttgt agagaccag gcctggagag tagacatttt gcctctgata    2400 agcactttt aaatggctct aagaataagc cacagcaaag aatttaaagt ggctccttta    2460
attggtgact tggagaaagc taggtcaagg gtttattata gcaccctctt gtattcctat    2520
ggcaatgcat ccttttatga aagtggtaca ccttaaagct tttatatgac tgtagcagag    2580
tatctggtga ttgtcaattc attccccta taggaataca aggggcacac agggaaggca    2640 gatccctag ttggcaagac tattttaact tgatacactg cagattcaga tgtgctgaaa    2700
gctctgcctc tggcttttccg gtcatgggtt ccagttaatt catgcctccc atggacctat    2760
ggagagcagc aagttgatct tagttaagtc tccctatatg agggataagt tcctgatttt    2820 tgttttatt tttgtgttac aaaagaaagc cctccctccc tgaacttgca gtaaggtcag    2880
cttcaggacc tgttccagtg ggcactgtac ttggatcttc ccggcgtgtg tgtgccttac    2940 acagggtga actgttcact gtggtgatgc atgatgaggg taaatggtag ttgaaaggag    3000
caggggccct ggtgttgcat ttagccctgg ggcatggagc tgaacagtac ttgtgcagga    3060
ttgttgtggc tactagagaa caagagggaa agtagggcag aaactggata cagttctgag    3120
gcacagccag acttgctcag ggtggccctg ccacaggctg cagctaccta ggaacattcc    3180
ttgcagaccc cgcattgccc tttggggggtg ccctgggatc cctggggtag tccagctctt    3240
cttcatttcc cagcgtggcc ctggttggaa gaagcagctg tcacagctgc tgtagacagc    3300
tgtgttccta caattggccc agcaccctgg ggcacgggag aagggtgggg accgttgctg    3360
tcactactca ggctgactgg ggcctggtca gattacgtat gcccttggtg gtttagagat    3420
aatccaaaat cagggtttgg tttggggaag aaaatcctcc cccttcctcc cccgccccgt    3480
tccctaccgc ctccactcct gccagctcat ttccttcaat ttcctttgac ctataggcta    3540 aaaagaaag gctcattcca gccacagggc agccttccct gggcctttgc ttctctagca    3600
caattatggg ttacttcctt tttcttaaca aaaagaatg tttgatttcc tctgggtgac    3660
cttattgtct gtaattgaaa ccctattgag aggtgatgtc tgtgttagcc aatgacccag    3720
gtgagctgct cggcttctc ttggtatgtc ttgtttggaa aagtggattt cattcatttc    3780
tgattgtcca gttaagtgat caccaaagga ctgagaatct gggagggcaa aaaaaaaaa    3840 aaagttttta tgtgcactta aatttgggga caatttatg tatctgtgtt aaggatatgt    3900
ttaagaacat aattctttg ttgctgtttg tttaagaagc accttagttt gtttaagaag    3960
caccttatat agtataatat atattttttt gaaattacat tgcttgttta tcagacaatt    4020
```

```
gaatgtagta attctgttct ggatttaatt tgactgggtt aacatgcaaa aaccaaggaa   4080
aaatatttag tttttttttt tttttttgta tactttcaa gctaccttgt catgtataca    4140
gtcatttatg cctaaagcct ggtgattatt catttaaatg aagatcacat ttcatatcaa   4200
cttttgtatc cacagtagac aaaatagcac taatccagat gcctattgtt ggatactgaa   4260
tgacagacaa tcttatgtag caaagattat gcctgaaaag gaaaattatt cagggcagct   4320
aattttgctt ttaccaaaat atcagtagta atatttttgg acagtagcta atgggtcagt   4380
gggttctttt taatgtttat acttagattt tcttttaaaa aaattaaaat aaaacaaaaa   4440
aaaatttcta ggactagacg atgtaatacc agctaaagcc aaacaattat acagtggaag   4500
gttttacatt attcatccaa tgtgtttcta ttcatgttaa gatactacta catttgaagt   4560
gggcagagaa catcagatga ttgaaatgtt cgcccagggg tctccagcaa ctttggaaat   4620
ctctttgtat ttttacttga agtgccacta atggacagca gatattttct ggctgatgtt   4680
ggtattgggt gtaggaacat gatttaaaaa aaaactcttg cctctgcttt cccccactct   4740
gaggcaagtt aaaatgtaaa agatgtgatt tatctggggg gctcaggtat ggtggggaag   4800
tggattcagg aatctgggga atggcaaata tattaagaag agtattgaaa gtatttggag   4860
gaaaatggtt aattctgggt gtgcaccagg gttcagtaga gtccacttct gccctggaga   4920
ccacaaatca actagctcca tttacagcca tttctaaaat ggcagcttca gttctagaga   4980
agaaagaaca acatcagcag taaagtccat ggaatagcta gtggtctgtg tttcttttcg   5040
ccattgccta gcttgccgta atgattctat aatgccatca tgcagcaatt atgagaggct   5100
aggtcatcca aagagaagac cctatcaatg taggttgcaa aatctaaccc ctaaggaagt   5160
gcagtctttg atttgatttc cctagtaacc ttgcagatat gtttaaccaa gccatagccc   5220 atgcctttg agggctgaac aaataaggga cttactgata atttacttt gatcacatta     5280 aggtgttctc accttgaaat cttatacact gaaatggcca ttgatttagg ccactggctt   5340
agagtactcc ttcccctgca tgacactgat tacaaatact ttcctattca tactttccaa   5400
ttatgagatg gactgtgggt actgggagtg atcactaaca ccatagtaat gtctaatatt   5460
cacaggcaga tctgcttggg gaagctagtt atgtgaaagg caaatagagt catacagtag   5520
ctcaaaaggc aaccataatt ctctttggtg caggtcttgg gagcgtgatc tagattacac    5580
tgcaccattc ccaagttaat cccctgaaaa cttactctca actggagcaa atgaactttg   5640
gtcccaaata tccatctttt cagtagcgtt aattatgctc tgtttccaac tgcatttcct   5700
ttccaattga attaaagtgt ggcctcgttt ttagtcattt aaaattgttt tctaagtaat   5760
tgctgcctct attatggcac ttcaattttg cactgtcttt tgagattcaa gaaaaatttc   5820
tattcttttt tttgcatcca attgtgcctg aacttttaaa atatgtaaat gctgccatgt   5880
tccaaaccca tcgtcagtgt gtgtgtttag agctgtgcac cctagaaaca acatattgtc   5940
ccatgagcag gtgcctgaga cacagacccc tttgcattca cagagaggtc attggttata   6000
gagacttgaa ttaataagtg acattatgcc agtttctgtt ctctcacagg tgataaacaa   6060 tgcttttgt gcactacata ctcttcagtg tagagctctt gttttatggg aaaaggctca    6120
aatgccaaat tgtgtttgat ggattaatat gcccttttgc cgatgcatac tattactgat   6180
gtgactcggt tttgtcgcag ctttgctttg tttaatgaaa cacacttgta aacctctttt   6240
gcactttgaa aaagaatcca gcgggatgct cgagcacctg taaacaattt tctcaaccta   6300
tttgatgttc aaataaagaa ttaaactaaa                                    6330
```

```
<210> SEQ ID NO 3
<211> LENGTH: 599
<212> TYPE: PRT
<213> ORGANISM: Mus musculus

<400> SEQUENCE: 3

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Met Pro Met Glu Arg Ala Leu Gly Glu Val Tyr Val Asp Asn Ser Lys
        35                  40                  45

Pro Thr Val Phe Asn Tyr Pro Glu Gly Ala Ala Tyr Glu Phe Asn Ala
    50                  55                  60

Ala Ala Ala Ala Ala Ala Ala Ser Ala Pro Val Tyr Gly Gln Ser
65                  70                  75                  80

Gly Ile Ala Tyr Gly Pro Gly Ser Glu Ala Ala Phe Ser Ala Asn
                85                  90                  95

Ser Leu Gly Ala Phe Pro Gln Leu Asn Ser Val Ser Pro Ser Pro Leu
            100                 105                 110

Met Leu Leu His Pro Pro Gln Leu Ser Pro Phe Leu His Pro His
        115                 120                 125

Gly Gln Gln Val Pro Tyr Tyr Leu Glu Asn Glu Pro Ser Ala Tyr Ala
130                 135                 140

Val Arg Asp Thr Gly Pro Pro Ala Phe Tyr Arg Ser Asn Ser Asp Asn
145                 150                 155                 160

Arg Arg Gln Asn Gly Arg Glu Arg Leu Ser Ser Asn Glu Lys Gly
                165                 170                 175

Asn Met Ile Met Glu Ser Ala Lys Glu Thr Arg Tyr Cys Ala Val Cys
            180                 185                 190

Asn Asp Tyr Ala Ser Gly Tyr His Tyr Gly Val Trp Ser Cys Glu Gly
        195                 200                 205

Cys Lys Ala Phe Phe Lys Arg Ser Ile Gln Gly His Asn Asp Tyr Met
    210                 215                 220

Cys Pro Ala Thr Asn Gln Cys Thr Ile Asp Lys Asn Arg Arg Lys Ser
225                 230                 235                 240

Cys Gln Ala Cys Arg Leu Arg Lys Cys Tyr Glu Val Gly Met Met Lys
                245                 250                 255

Gly Gly Ile Arg Lys Asp Arg Arg Gly Gly Arg Met Leu Lys His Lys
            260                 265                 270

Arg Gln Arg Asp Asp Leu Glu Gly Arg Asn Glu Met Gly Ala Ser Gly
        275                 280                 285

Asp Met Arg Ala Ala Asn Leu Trp Pro Ser Pro Leu Val Ile Lys His
    290                 295                 300

Thr Lys Lys Asn Ser Pro Ala Leu Ser Leu Thr Ala Asp Gln Met Val
305                 310                 315                 320

Ser Ala Leu Leu Asp Ala Glu Pro Pro Met Ile Tyr Ser Glu Tyr Asp
                325                 330                 335

Pro Ser Arg Pro Phe Ser Glu Ala Ser Met Met Gly Leu Leu Thr Asn
            340                 345                 350

Leu Ala Asp Arg Glu Leu Val His Met Ile Asn Trp Ala Lys Arg Val
        355                 360                 365

Pro Gly Phe Gly Asp Leu Asn Leu His Asp Gln Val His Leu Leu Glu
    370                 375                 380
```

```
Cys Ala Trp Leu Glu Ile Leu Met Ile Gly Leu Val Trp Arg Ser Met
385                 390                 395                 400

Glu His Pro Gly Lys Leu Leu Phe Ala Pro Asn Leu Leu Leu Asp Arg
                405                 410                 415

Asn Gln Gly Lys Cys Val Glu Gly Met Val Glu Ile Phe Asp Met Leu
                420                 425                 430

Leu Ala Thr Ser Ser Arg Phe Arg Met Met Asn Leu Gln Gly Glu Glu
                435                 440                 445

Phe Val Cys Leu Lys Ser Ile Ile Leu Leu Asn Ser Gly Val Tyr Thr
450                 455                 460

Phe Leu Ser Ser Thr Leu Lys Ser Leu Glu Glu Lys Asp His Ile His
465                 470                 475                 480

Arg Val Leu Asp Lys Ile Thr Asp Thr Leu Ile His Leu Met Ala Lys
                485                 490                 495

Ala Gly Leu Thr Leu Gln Gln Gln His Arg Arg Leu Ala Gln Leu Leu
                500                 505                 510

Leu Ile Leu Ser His Ile Arg His Met Ser Asn Lys Gly Met Glu His
                515                 520                 525

Leu Tyr Asn Met Lys Cys Lys Asn Val Val Pro Leu Tyr Asp Leu Leu
530                 535                 540

Leu Glu Met Leu Asp Ala His Arg Leu His Ala Pro Ala Ser Arg Met
545                 550                 555                 560

Gly Val Pro Pro Glu Glu Pro Ser Gln Thr Gln Leu Ala Thr Thr Ser
                565                 570                 575

Ser Thr Ser Ala His Ser Leu Gln Thr Tyr Tyr Ile Pro Pro Glu Ala
                580                 585                 590

Glu Gly Phe Pro Asn Thr Ile
        595

<210> SEQ ID NO 4
<211> LENGTH: 4319
<212> TYPE: DNA
<213> ORGANISM: Mus musculus

<400> SEQUENCE: 4
acaaggctcc ctgctcagca gccttgtgat gccaggagag gccaatgccc cctcctctgc    60
cattgtctag cttaagaagg cagtctctgg gcgacattct tctcaagcag gtggcccacg   120
cgctgctgag ccctctgcgt gcgcggggag ccagtctgta actcgccggc tgccacttac   180
catgaccatg acccttcaca ccaaagcctc gggaatggcc ttgctgcacc agatccaagg   240
gaacgagctg gagcccctca accgcccgca gctcaagatg cccatggaga gggccctggg   300
cgaggtatac gtggacaaca gcaagcccac tgtgttcaac tacccccgagg gcgccgccta   360
cgagttcaac gccgccgccg ccgccgccgc cgccgcctcg gcgccggtct acggccagtc   420
gggcatcgcc tacggccccg ggtcggaggc ggccgccttc agtgccaaca gcctgggggc   480
tttcccccag ctcaacagcg tgtcgcctag cccgctgatg ctgctgcacc cgccgccgca   540
gctgtctcct ttcctgcacc cgcacggcca gcaggtgccc tactacctgg agaacgagcc   600
cagcgcctac gccgtgcgcg caccggccc tcccgccttc acaggtctga ttctgacaa   660
tcgacgccag aatggccgag agagactgtc cagcagtaac gagaaggaa acatgatcat   720
ggagtctgcc aaggagactc gctactgtgc cgtgtgcaat gactatgcct ctggctacca   780
ttatggggtc tggtcctgcg aaggctgcaa ggcttctctt aagagaagca ttcaaggaca   840
caatgactac atgtgtccag ctacaaacca atgcaccatt gacaagaacc ggaggaagag   900
```

```
ttgccaggcc tgtcggctgc gcaagtgtta cgaagtgggc atgatgaaag gcggcatacg    960
gaaagaccgc cgaggaggga gaatgttgaa gcacaagcgt cagagagatg acttggaagg   1020
ccgaaatgaa atgggtgctt caggagacat gagggctgcc aacctttggc caagccctct   1080
tgtgattaag cacactaaga agaatagccc tgccttgtcc ttgacagctg accagatggt   1140
cagtgccttg ttggatgctg aaccgcccat gatctattct gaatatgatc cttctagacc   1200
cttcagtgaa gcctcaatga tgggcttatt gaccaaccta gcagataggg agctggttca   1260
tatgatcaac tgggcaaaga gagtgccagg ctttgggac ttgaatctcc atgatcaggt    1320
ccaccttctc gagtgtgcct ggctggagat tctgatgatt ggtctcgtct ggcgctccat   1380
ggaacacccg gggaagctcc tgtttgctcc taacttgctc ctggacagga atcaaggtaa   1440
atgtgtggaa ggcatggtgg agatctttga catgttgctg gctacgtcaa gtcggttccg   1500
catgatgaac ctgcagggag aagagtttgt gtgcctcaaa tccatcattt tgcttaattc   1560
cggagtgtac acgtttctgt ccagcacctt gaagtctctg gaagagaagg accacatcca   1620
ccgtgtcctg gacaagatca cagacacttt gatccacctg atggccaaag ctggcctgac   1680
tctgcagcag cagcatcgcc gcctagctca gctccttctc attctttccc atatccggca   1740
catgagtaac aaaggcatgg agcatctcta caacatgaaa tgcaagaacg ttgtgccct    1800
ctatgacctg ctcctggaga tgttggatgc ccaccgcctt catgcccag ccagtcgcat    1860
gggagtgccc ccagaggagc ccagccagac ccagctggcc accaccagct ccacttcagc   1920
acattcctta caaacctact acatacccc ggaagcagag ggcttcccca cacgatctg    1980
agagctccca ggctccccga aaggttctga gaatccctgc aacattttac ccatgtcatg   2040
tatgactagc agaattctgt ctcctgcgta cactgtggca tgcatccacc accagtggct   2100
ttctagtatg agtggccatt tatttgcttg ctcagttctt agtggcatgt cttctgttgg   2160
gaacaggcaa aagggattcc agggctaaat cttggtaaca gctctctttc tccctttgct   2220
acgtcactaa ctatgaggat tcctatagtc ttcagtcttc atgaatgaat tgagataact   2280
gcattgaagc tacttgttga gacccaagcc tagagagtaa acatttcacc tctgataagc   2340
acttcataat ggctccaaga ggaagcctca gcaaagactt caaagtggct cctttaattg   2400
aagtcgttga caaagcgatc tcatggcttc ctaatagcac ccgcttgcat tcctatagca   2460
acatgtgact ttattaaagg gaatcttga gcccctatag gaatatgtga tgcacacaga    2520
aaaggaagat gcccccagtt gtcaagacca tgtcaactca atacagtcaa ccttttcact   2580
tcttaaagtg tcagctgccg agtattatat acatggtggg ttctagacaa ttcttgcttc   2640
ccatgacttg tgggaaacag aaagtctatt tcagttaata ccctggaatg aattagtctc   2700
cttcatgagg gctgtagggt gtgttgattt taatttgatt tcattttata atagtcttct   2760
gccctgggg cttgcagtaa aggcagcttg aggacctgtt ctggtaaact ggacattctt    2820
cagcacagga tgctagcctt gtctcttccc tgatgtcaat tgccctaaat tgttaccatg   2880
tagattgatc aagggcagtc acaatgaacc tgcaagctgg tgacaatttt ttggtttgtt   2940
tagtttatt cttgggggca gggaacaagt aatgtatggg caatgactgt gactcggagg    3000
agtctaagaa ggaaagtaag ggagaaatgt ggagaatgac ctggccaggg cagcagcttc   3060
ccagaggtgc acctcacaga tcccaccatg cacagtgagg ctgctctggg atccatgggc   3120
tgacttcact tacatttcag gtatgagcct gattggaaga ggtgacatca gatacctgtg   3180
ttcctgtaga tgctccagga acttggggaa aggcatgggg gcaagatctt ggagcactca   3240
tgactcaagc tgttgagaag ttgctcagac tagactgtgc ttgattattc tgaactcatc   3300
```

-continued

```
caaaaaccag ctagtgagat cttggggaga aaaatttctt cctcaacaca gttcatgatc    3360
ttaaattttg taaactagaa atgatgaatg accagaattg ggtcatgaga gtcctttgaa    3420
caagggata aaaggaaga cttactctat ccacagccac ccaagacctc tggggtcttg      3480
gtctctctag tacaactaag gattacttcc ttttccaaac caaatgaaa gttcagtttc     3540
catcccggac ttcatgatct ataatttgaa ctccattgag atatgatggg ttagccaaaa   3600
cctaggtgaa tggctaggct tctcttggcc tgtactttt ggaatggtgg gttccattaa    3660
tttctgctct cccagttaac tgactatcaa agatgtggaa actgggagag ccaatttttc   3720
ttcttatttt ttttaaattt ctcatacttg ttcatcaaat tcaaggacaa ttttatgtat   3780
atgctttaag aacatgttta agaacctaac tcttttgttt gtgtttaaga agcaccttat   3840
atagtataat atatattttt gttgaagttt aattgcttgt ttattggaca attgaatgta   3900
atagttatgt tctgagtttt aatttgattg ggtttaacac tgcaaaagcc aaggggaaaa   3960
tatttagttt gttttttttt ttttttttg tagacgtttc aaactaccgt gtcatgtatg    4020
cagttattaa tgcctaaagc cttgtgattt tcatttaaat gaagatcaca tttcgtatca   4080
acttttgtat ccacagtaga caaaatagaa ggaatccaca tgcctattgc tgggtgttga   4140
atgacagaca atcttatgta gcagagatta tgcctgggaa ggaaaattat tcagggcagc   4200
taattttgct tttaccaaaa tatctgtagt aatattttg gacagtagct aatgggtcag    4260
tgggttcttt ttaatgttta tactgagatt tttcttttac aaaaataaaa acaaaaatt    4319
```

<210> SEQ ID NO 5
<211> LENGTH: 600
<212> TYPE: PRT
<213> ORGANISM: Rattus norvegicus

<400> SEQUENCE: 5

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Met Pro Met Glu Arg Ala Leu Gly Glu Val Tyr Val Asp Asn Ser Lys
        35                  40                  45

Pro Ala Val Phe Asn Tyr Pro Glu Gly Ala Ala Tyr Glu Phe Asn Ala
    50                  55                  60

Ala Ala Ala Ala Ala Ala Gly Ala Ser Ala Pro Val Tyr Gly Gln
65                  70                  75                  80

Ser Ser Ile Thr Tyr Gly Pro Gly Ser Glu Ala Ala Phe Gly Ala
                85                  90                  95

Asn Ser Leu Gly Ala Phe Pro Gln Leu Asn Ser Val Ser Pro Ser Pro
            100                 105                 110

Leu Met Leu Leu His Pro Pro His Val Ser Pro Phe Leu His Pro
        115                 120                 125

His Gly His Gln Val Pro Tyr Tyr Leu Glu Asn Glu Pro Ser Ala Tyr
    130                 135                 140

Ala Val Arg Asp Thr Gly Pro Pro Ala Phe Tyr Arg Ser Asn Ser Asp
145                 150                 155                 160

Asn Arg Arg Gln Asn Gly Arg Glu Arg Leu Ser Ser Ser Glu Lys
                165                 170                 175

Gly Asn Met Ile Met Glu Ser Ala Lys Glu Thr Arg Tyr Cys Ala Val
            180                 185                 190
```

-continued

```
Cys Asn Asp Tyr Ala Ser Gly Tyr His Tyr Gly Val Trp Ser Cys Glu
            195                 200                 205
Gly Cys Lys Ala Phe Phe Lys Arg Ser Ile Gln Gly His Asn Asp Tyr
        210                 215                 220
Met Cys Pro Ala Thr Asn Gln Cys Thr Ile Asp Lys Asn Arg Arg Lys
225                 230                 235                 240
Ser Cys Gln Ala Cys Arg Leu Arg Lys Cys Tyr Glu Val Gly Met Met
            245                 250                 255
Lys Gly Gly Ile Arg Lys Asp Arg Arg Gly Gly Arg Met Leu Lys His
        260                 265                 270
Lys Arg Gln Arg Asp Asp Leu Glu Gly Arg Asn Glu Met Gly Thr Ser
        275                 280                 285
Gly Asp Met Arg Ala Ala Asn Leu Trp Pro Ser Pro Leu Val Ile Lys
        290                 295                 300
His Thr Lys Lys Asn Ser Pro Ala Leu Ser Leu Thr Ala Asp Gln Met
305                 310                 315                 320
Val Ser Ala Leu Leu Asp Ala Glu Pro Pro Leu Ile Tyr Ser Glu Tyr
            325                 330                 335
Asp Pro Ser Arg Pro Phe Ser Glu Ala Ser Met Met Gly Leu Leu Thr
        340                 345                 350
Asn Leu Ala Asp Arg Glu Leu Val His Met Ile Asn Trp Ala Lys Arg
        355                 360                 365
Val Pro Gly Phe Gly Asp Leu Asn Leu His Asp Gln Val His Leu Leu
    370                 375                 380
Glu Cys Ala Trp Leu Glu Ile Leu Met Ile Gly Leu Val Trp Arg Ser
385                 390                 395                 400
Met Glu His Pro Gly Lys Leu Leu Phe Ala Pro Asn Leu Leu Leu Asp
            405                 410                 415
Arg Asn Gln Gly Lys Cys Val Glu Gly Met Val Glu Ile Phe Asp Met
        420                 425                 430
Leu Leu Ala Thr Ser Ser Arg Phe Arg Met Met Asn Leu Gln Gly Glu
        435                 440                 445
Glu Phe Val Cys Leu Lys Ser Ile Ile Leu Leu Asn Ser Gly Val Tyr
    450                 455                 460
Thr Phe Leu Ser Ser Thr Leu Lys Ser Leu Glu Glu Lys Asp His Ile
465                 470                 475                 480
His Arg Val Leu Asp Lys Ile Asn Asp Thr Leu Ile His Leu Met Ala
            485                 490                 495
Lys Ala Gly Leu Thr Leu Gln Gln Gln His Arg Arg Leu Ala Gln Leu
        500                 505                 510
Leu Leu Ile Leu Ser His Ile Arg His Met Ser Asn Lys Gly Met Glu
        515                 520                 525
His Leu Tyr Asn Met Lys Cys Lys Asn Val Val Pro Leu Tyr Asp Leu
    530                 535                 540
Leu Leu Glu Met Leu Asp Ala His Arg Leu His Ala Pro Ala Ser Arg
545                 550                 555                 560
Met Gly Val Pro Pro Glu Glu Pro Ser Gln Ser Gln Leu Thr Thr Thr
            565                 570                 575
Ser Ser Thr Ser Ala His Ser Leu Gln Thr Tyr Tyr Ile Pro Pro Glu
        580                 585                 590
Ala Glu Gly Phe Pro Asn Thr Ile
    595                 600
```

<210> SEQ ID NO 6
<211> LENGTH: 2090
<212> TYPE: DNA
<213> ORGANISM: Rattus norvegicus

<400> SEQUENCE: 6

| | | | | | |
|---|---|---|---|---|---|
| ccacacacgc | tctgccttga | tcacacaccg | cgccactcga | tcattcgagc | acattccttc | 60 |
| cttccgtctt | actgtctcag | ctcttgactt | ctacaaaccc | atggaacatt | tctggaaaga | 120 |
| cgcttttgaa | ccagcagggt | ggctcatccg | ctgctgagcc | ctctgcgtgc | gcggaagcc | 180 |
| aatctgtacc | tcggcggctg | ccactgacca | tgaccatgac | ccttcacacc | aaagcctcgg | 240 |
| gaatggcctt | gttgcaccag | atccaaggga | acgagctgga | gcccctcaat | cgcccgcagc | 300 |
| tcaagatgcc | catggagagg | gctctgggcg | aggtgtacgt | ggacaacagc | aagcccgccg | 360 |
| tgttcaacta | ccccgagggc | gccgcctacg | agttcaacgc | gccgccgcc | gccgcggccg | 420 |
| ccggggcctc | ggctccggtc | tatggccagt | cgagcatcac | ttacggtccg | ggtccgagg | 480 |
| cggccgcctt | tggtgccaat | agtctggggg | ctttcccca | gctcaacagc | gtgtcgccca | 540 |
| gtccgctgat | gctgctgcac | ccgccgccgc | acgtgtcgcc | gttcctgcac | ccgcatggcc | 600 |
| accaggtgcc | ctactacctg | gagaacgagc | ccagcgccta | cgctgtacgc | gacaccggcc | 660 |
| ctccccgcctt | ctacaggtcc | aattctgaca | atcgacgcca | gaatggccga | gagagactct | 720 |
| ccagcagcag | cgagaaggga | aacatgatca | tggagtctgc | caaggagact | cgctactgtg | 780 |
| ctgtgtgtaa | cgactatgcc | tctggctacc | attatgggt | ctggtcctgt | gaaggctgca | 840 |
| aggctttctt | taagagaagc | attcaaggac | ataatgacta | catgtgtcca | gctacaaacc | 900 |
| aatgcaccat | cgataagaac | cggaggaaga | gttgccaggc | ctgccggctg | cgcaagtgtt | 960 |
| acgaagtggg | catgatgaaa | ggcgggatac | gaaaagaccg | ccgaggaggg | agaatgttga | 1020 |
| agcacaagcg | tcagagagat | gacttggaag | gccgaaatga | aatgggcact | tcaggagaca | 1080 |
| tgagagctgc | caacctttgg | ccaagtccac | ttgtgatcaa | gcacactaag | aagaatagcc | 1140 |
| ccgccctgtc | cttgacagct | gaccagatgg | tcagtgcctt | attggatgct | gaaccacctt | 1200 |
| tgatctattc | tgaatatgat | ccttctagac | ccttcagtga | agcctcaatg | atgggcttat | 1260 |
| tgaccaacct | ggcagacagg | gagctggttc | atatgatcaa | ctgggcaaag | agagtgccag | 1320 |
| gctttgggga | cttgaatctc | cacgatcaag | ttcaccttct | ggagtgtgcc | tggttggaga | 1380 |
| tcctgatgat | tggtctggtc | tggcgctcca | tggaacaccc | ggggaagctc | ctgtttgctc | 1440 |
| ctaacttgct | cttggacagg | aatcaaggta | aatgtgtaga | aggcatggtg | gagatctttg | 1500 |
| acatgttgct | ggctacgtca | agtcgattcc | gcatgatgaa | cctgcaggga | aagagtttg | 1560 |
| tgtgcctcaa | atcaatcatt | ttgcttaatt | ctggagtgta | cacatttcta | tccagcacct | 1620 |
| tgaagtctct | ggaagagaag | gaccacatcc | accgagtcct | ggacaagatc | aacgacactt | 1680 |
| tgatccactt | gatggccaaa | gctggcctga | ctctgcagca | acagcatcgc | cgtctggccc | 1740 |
| agctcctcct | catcctttcc | catatccggc | acatgagtaa | caaggcatg | gagcatctct | 1800 |
| acaacatgaa | atgcaagaat | gtcgtgcctc | tctatgacct | gctgctggag | atgctggatg | 1860 |
| ctcatcgtct | tcatgccccc | gccagtcgca | tgggagtgcc | cccggaggag | cctagccaga | 1920 |
| gccagctgac | caccaccagc | tccacttcag | cacattcctt | acaaacctac | tacatccccc | 1980 |
| cggaagcaga | gggcttcccc | aacaccatct | gagaactccc | aggctcccca | caaggttctg | 2040 |
| cgaatccctg | aaacgttttta | cccatgtcct | gtatgacttt | agcagaattc | 2090 |

PHOTOACTIVATABLE CAGED TAMOXIFEN AND TAMOXIFEN DERIVATIVE MOLECULES AND METHODS OF USE THEREOF

CROSS-REFERENCE TO RELATED APPLICATIONS

This application is the U.S. National Phase of International Application No. PCT/US2013/031165 filed Mar. 14, 2013, which claims priority to U.S. Provisional Patent Application Ser. No. 61/635,068, filed Apr. 18, 2012, both of which are incorporated by reference herein.

FEDERALLY SPONSORED RESEARCH

This invention was made with Government support under Grant Numbers CA141508, CA086355, CA092782, CA117969, HL070831, and SN268201 awarded by the National Institutes of Health. The Government has certain rights in the invention.

BACKGROUND OF THE INVENTION

Spatial and temporal genetic control is necessary to better dissect the role of specific genes and cell populations in development, disease, and therapy. Site-specific recombination mediated by Cre recombinase is a powerful genetic tool to manipulate genetic elements in model organisms (Nagy, *Genesis* 26:99, 2000). When placed under the control of a tissue-specific promoter, Cre/LoxP-mediated recombination allows tissue-specific investigation of gene functions (Nagy, *Genesis* 26:99, 2000). Fusing Cre with a mutant form of the estrogen receptor (ER) ligand binding domain further enables temporal control of recombination (Nagy, *Genesis* 26:99, 2000). While this conditional CreER system allows for temporal control, the spatial control through tissue-specific promoters is limited by relatively broad activation in all target cells, non-specificity of many of such cell type-'specific' promoters, and/or the lack of validated promoters in certain cell types.

SUMMARY OF THE INVENTION

The invention is based, in part, on the discovery that conjugation of tamoxifen or tamoxifen derivatives to photoactivatable caged molecules (e.g., 1-(4,5-dimethoxy-2-nitrophenyl)ethyl (DMNPE)) results in a sensitive and specific optical release of tamoxifen or tamoxifen derivatives to eukaryotic (e.g., mammalian, plant, yeast, nematode, parasite, or reptile) cells following irradiation. In view of this discovery, provided herein are compositions containing photoactivatable caged tamoxifen and caged tamoxifen derivative molecules, and methods of optically inducing nuclear translocation of a fusion protein containing a mammalian estrogen receptor ligand binding domain in a eukaryotic (e.g., mammalian, plant, yeast, nematode, parasite, or reptile) cell and methods of optically inducing recombination in a eukaryotic (e.g., mammalian, plant, yeast, nematode, parasite, or reptile) cell that include contacting a eukaryotic cell with at least one of these compositions. Also provided are methods of treating breast cancer in a subject that include administering a photoactivatable caged tamoxifen or caged tamoxifen derivative molecule to a subject having breast cancer.

Provided herein are compositions containing:

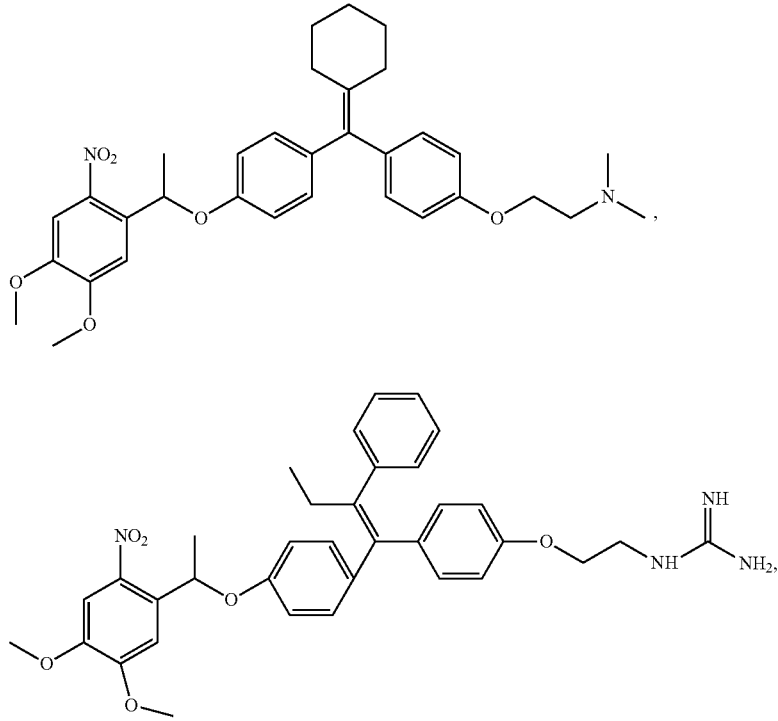

-continued
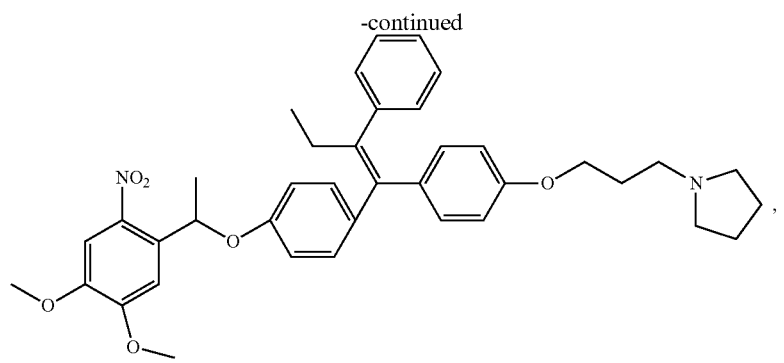
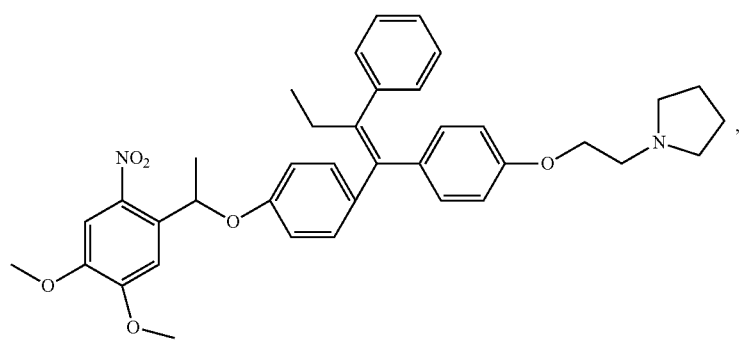
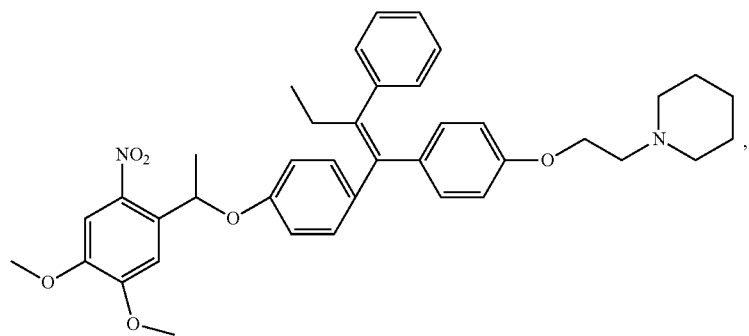
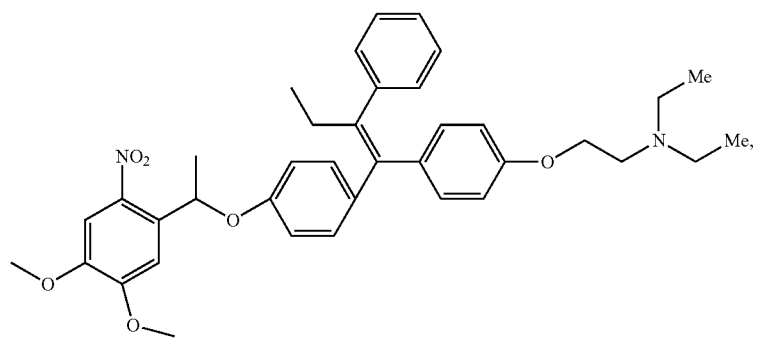
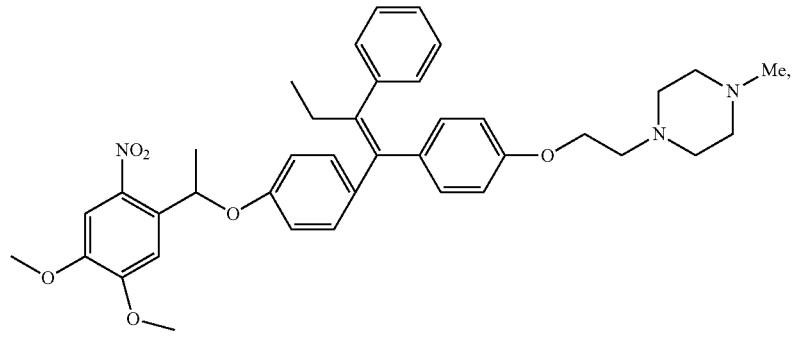

-continued

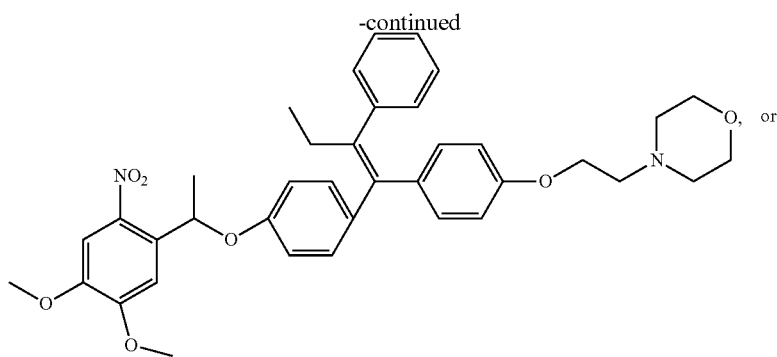

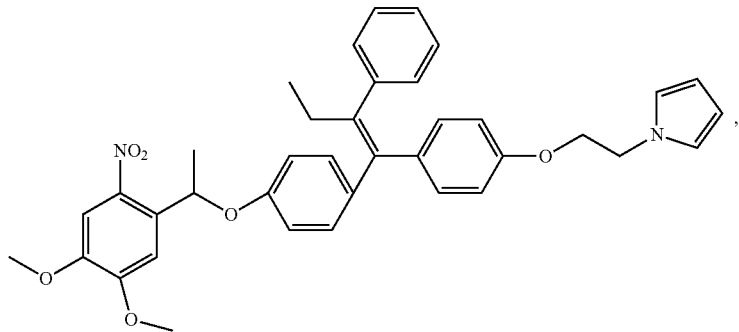 [SMILES: CC/C(=C(/c1ccc(OCCn2cccc2)cc1)c1ccc(OC(C)c2cc(OC)c(OC)cc2[N+](=O)[O-])cc1)c1ccccc1]

or a pharmaceutically acceptable salt thereof.

In some embodiments, the composition further contains a physiologically acceptable excipient or buffer. In some embodiments, the composition is formulated as a liquid. In some embodiments, the composition is formulated for intravenous, intaarterial, transdermal, intramuscular, intraperitoneal, subcutaneous, intrathecal, interductal, periductal, or ocular administration. In some embodiments, the composition is formulated as a solid. In some embodiments, the composition is formulated as a gel. In some embodiments, the composition is formulated for oral administration.

In some embodiments, the composition contains at least 80% by weight of

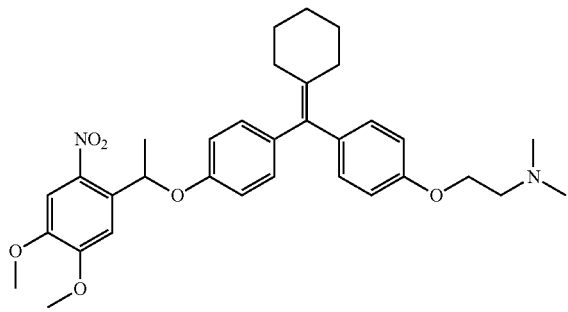 [SMILES: COc1cc(C(C)Oc2ccc(C(=C3CCCCC3)c3ccc(OCCN(C)C)cc3)cc2)c([N+](=O)[O-])cc1OC]

or a pharmaceutically acceptable salt thereof.

Also provided are kits containing one or more doses of any of the compositions described herein; and a light source that emits light of a wavelength of between 350 nm to 410 nm.

Also provided are methods of inducing nuclear translocation of a fusion protein containing a human estrogen receptor ligand binding domain in a eukaryotic cell that include providing a eukaryotic cell that contains a fusion protein containing a human estrogen receptor ligand binding domain, contacting the eukaryotic cell with any of the compositions described herein; and irradiating the eukaryotic cell with a wavelength of light between 350 nm to 410 nm for a period of time sufficient to release 4-hydroxycyclofen from the composition, where the released 4-hydroxycyclofen induces the nuclear translocation of the fusion protein. In some embodiments, the eukaryotic cell is in vitro. Some embodiments further include administering the irradiated eukaryotic cell to a mammal. In some embodiments, the eukaryotic cell is in a mammal (e.g., a mouse or rat). In some embodiments, the eukaryotic cell is present in the mammary gland or the skin. In some embodiments, the composition is locally administered to a target tissue in the mammal that contains the eukaryotic cell. In some embodiments, the composition is administered to the mammal via oral, intravenous, intaarterial, transdermal, intramuscular, intraperitoneal, subcutaneous, intrathecal, interductal, periductal, nasal, or ocular administration.

In some embodiments, the eukaryotic cell contains a nucleic acid encoding the fusion protein, and the nucleic acid is stably integrated into a chromosome of the cell. In some embodiments, the nucleic acid encoding the fusion protein is operably linked to a tissue-specific promoter sequence. In some embodiments, the nucleic acid encoding the fusion protein is operably linked to a ubiquitous promoter. In some embodiments, the nucleic acid encoding the fusion protein is operably linked to an inducible promoter sequence, and the eukaryotic cell is further contacted with a chemical inducing agent.

In some embodiments, the fusion protein contains a sequence of a recombinase, and the fusion protein has recombinase enzymatic activity. In some embodiments, the recombinase is Cre recombinase. In some embodiments, the fusion protein contains a sequence of a transcription factor, and the fusion protein is capable of promoting gene transcription in the nucleus of the eukaryotic cell. In some embodiments, the fusion protein promotes gene transcription of a gene that is present in a recombinant gene construct that is integrated into a chromosome of the eukaryotic cell. In some embodiments, the fusion protein contains a sequence of a transcription repressor, and the fusion protein is capable of repressing transcription of a gene in the nucleus of the eukaryotic cell. In some embodiments, the fusion protein represses the transcription of a gene that is present in a recombinant gene construct that is integrated into a chromosome of the eukaryotic cell.

In some embodiments, the fusion protein contains a sequence of a histone deacetylase, a histone acetyltransferase, or an O-6-methylguanine-DNA methyltransferase, and the fusion protein has histone deacetylase, histone acetyltransferase, or O-6-methylguanine-DNA methyltransferase activity, respectively. In some embodiments, the fusion protein contains a sequence of a telomerase, and the fusion protein has telomerase activity. In some embodiments, the fusion protein contains a sequence of an oncogene.

In some embodiments, the eukaryotic cell is an epithelial cell, an endothelial cell, a muscle cell, an adipose cell, a bone cell, a cartilage cell, or a neuron. In some embodiments, the eukaryotic cell is an undifferentiated cell, and the fusion protein comprises a sequence of a transcription factor or transcription repressor that induces cellular differentiation. In some embodiments, the irradiating is performed for less than a total of 15 minutes. In some embodiments, the contacting and irradiating occur within 24 hours of each other. In some embodiments, the contacting and irradiating occur within 6 hours of each other. In some embodiments, the contacting and irradiating occur within 1 hour of each other.

Also provided are methods of inducing recombination in a eukaryotic cell that include: providing a eukaryotic cell that contains (i) a nucleic acid encoding a fusion protein containing a sequence of a recombinase and a sequence of a human estrogen receptor ligand binding domain, where the fusion protein has recombinase activity, and (ii) a recombinase recognition sequence that is specifically recognized by the fusion protein, where both the nucleic acid encoding the fusion protein and the recombinase recognition sequence are integrated into a chromosome within the nucleus of the eukaryotic cell; contacting the eukaryotic cell any of the compositions described herein; and irradiating the eukaryotic cell with a wavelength of light between 350 nm to 410 nm for a period of time sufficient to release 4-hydroxycyclofen from the composition, where the 4-hydroxycyclofen stimulates the nuclear importation of the fusion protein and the fusion protein stimulates recombination at the recombinase recognition sequence. In some embodiments, the eukaryotic cell is in vitro. In some embodiments, the eukaryotic cell is in a mammal. In some embodiments, the mammal is a mouse or rat. In some embodiments, the eukaryotic cell is present in the mammary gland or the skin. In some embodiments, the composition is locally administered to a target tissue in the mammal that contains the eukaryotic cell. In some embodiments, the composition is administered to the mammal via oral, intravenous, intaarterial, transdermal, intramuscular, intraperitoneal, subcutaneous, intrathecal, interductal, periductal, nasal, or ocular administration.

In some embodiments, the recombinase is Cre recombinase. In some embodiments, the recombination results in a decrease in the expression of a transgene located between two recombinase recognition sequences in the chromosome. In some embodiments, the recombination results in the replacement of a sequence between two recombinase recognition sequences with a new transgenic sequence. In some embodiments, the recombination results in the increase in the proximity of a promoter or enhancer sequence to a transgene, wherein the recombination results in increased expression of the transgene.

In some embodiments, the nucleic acid encoding the fusion protein is operably linked to tissue specific promoter sequence in the chromosome of the eukaryotic cell. In some embodiments, the nucleic acid encoding the fusion protein is operably linked to an inducible promoter in the chromosome of the eukaryotic cell, and the eukaryotic cell is further contacted with a chemical inducing agent. In some embodiments, the nucleic acid encoding the fusion protein is operably linked to a ubiquitous promoter in the chromosome of the eukaryotic cell.

In some embodiments, the composition is administered to the animal by systemic administration and a specific tissue of the mammal is irradiated. In some embodiments, the contacting and irradiating occur within 24 hours of each other. In some embodiments, the contacting and irradiating occur within 6 hours of each other. In some embodiments, the contacting and irradiating occur within 1 hour of each other. In some embodiments, the irradiating is performed using an endoscopic light source.

Also provided are compositions that contain:

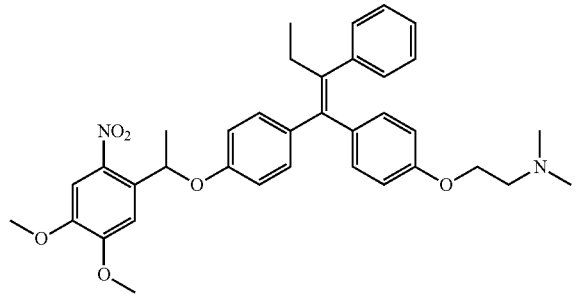

or a pharmaceutically acceptable salt thereof.

In some embodiments, the composition further comprises at least one additional breast cancer therapeutic. In some embodiments, the composition further contains a physiologically acceptable excipient or buffer. In some embodiments, the composition is formulated as a liquid. In some embodiments, the composition is formulated for intravenous, intaarterial, transdermal, intramuscular, intraperitoneal, subcutaneous, intrathecal, interductal, periductal, or ocular administration. In some embodiments, the composition is formulated as a solid. In some embodiments, the composition is formulated as a gel. In some embodiments, the composition is formulated for oral administration.

Also provided are methods of treating breast cancer in a subject that include: administering to the subject an amount of any of the compositions described herein sufficient to treat breast cancer in a subject; and irradiating the mammary tissue of the subject with light between 200 nm and 900 nm, wherein the irradiating mediates the release of 4-hydroxytamoxifen in the irradiated mammary tissue. In some embodiments, the subject is diagnosed as having breast cancer. In some embodiments, the composition is locally administered to the mammary tissue of the subject. In some embodiments, the composition is systemically administered to the subject. In some embodiments, the composition is administered to the mammal via oral, intravenous, intaarterial, transdermal, intramuscular, intraperitoneal, subcutaneous, intrathecal, interductal, periductal, nasal, or ocular administration. In some embodiments, the contacting and irradiating occur within 24 hours of each other. In some embodiments, the contacting and irradiating occur within 6 hours of each other. In some embodiments, the contacting and irradiating occur within 1 hour of each other. Some embodiments further include administering to the subject one or more additional breast cancer therapeutics.

Also provided are kits containing one or more doses of any of the compositions described herein; and a light source that emits light of a wavelength of between 200 nm to 900 nm.

By the term "mammalian estrogen receptor ligand binding domain" is meant a contiguous sequence of amino acids that is at least 80% (e.g., at least 85%, 90%, 95%, 96%, 97%, 98%, 99%, or 100%) identical to the sequence of the ligand binding domain of a mammalian (e.g., human, mouse, or rat) estrogen receptor that has the ability to bind to tamoxifen or a tamoxifen derivative (e.g., 4-hydroxycyclofen). Non-limiting exemplary mammalian receptor ligand binding domains are described herein. Methods for determining the ability of a mammalian estrogen receptor ligand binding domain to bind tamoxifen or a tamoxifen derivative are described herein.

By the term "human estrogen receptor ligand binding domain" is meant a contiguous sequence of amino acids that is at least 80% (e.g., at least 85%, 90%, 95%, 96%, 97%, 98%, 99%, or 100%) identical to the sequence of the ligand binding domain of a human estrogen receptor that has the ability to bind to tamoxifen or a tamoxifen derivative (e.g., 4-hydroxycyclofen). Non-limiting examples of human estrogen receptor ligand binding domains are described herein. Additional examples of human estrogen receptor ligand binding domains are known in the art. In some embodiments, the human estrogen receptor ligand binding domain contains a sequence at least 80% (e.g., at least 85%, 90%, 96%, 97%, 98%, 99%, or 100%) identical to amino acids 310 to 547 of SEQ ID NO: 1. Methods for determining the ability of a human estrogen receptor ligand binding domain to bind tamoxifen or a tamoxifen derivative are described herein.

By the term "estrogen receptor fusion protein," "ER fusion protein," or "fusion protein containing an ER ligand binding domain" is meant a polypeptide sequence containing a mammalian estrogen receptor ligand binding domain (e.g., a human estrogen receptor ligand binding domain) and at least one additional polypeptide sequence (a fusion partner polypeptide). Non-limiting examples of fusion partner polypeptides are described herein. Additional examples of fusion partner polypeptides are known in the art. In some embodiments, the fusion partner polypeptide can be derived from a mammal (e.g., the same or a different mammal), a bacterium, a virus, or a parasite. In some embodiments, the mammalian estrogen receptor ligand binding domain can be located at the N-terminus of the ER fusion protein or can be located N-terminal to the fusion partner polypeptide. In some embodiments, the mammalian estrogen receptor ligand binding domain can be located at the C-terminus of the ER fusion protein or can be located C-terminal to the fusion partner polypeptide. In some embodiments, there can be an intervening amino acid sequence between the mammalian estrogen receptor ligand binding domain and the fusion partner polypeptide.

By the term "caged tamoxifen molecule" is meant a molecule containing tamoxifen conjugated to a photoactivatable caging molecule (e.g., 1-(4,5-dimethoxy-2-nitrophenyl) ethanol (DMNPE)) that releases tamoxifen upon exposure to light. Additional examples of photoactivatable caging molecules that can be present in caged tamoxifen molecules are described herein. In some embodiments, there is a linking group present between the tamoxifen and the photoactivatable caging molecule. In some embodiments, the tamoxifen and the photoactivatable caging molecule are joined by an ester, an ether, an amido group, a carbonate, a carbamate, or an acetal.

By the term "caged tamoxifen derivative molecule" is meant a molecule containing tamoxifen derivative (e.g., 4-hydroxy tamoxifen or 4-hydroxycyclofen) conjugated to a photoactivatable caging molecule (e.g., 1-(4,5-dimethoxy-2-nitrophenyl) ethanol (DMNPE)) that releases the tamoxifen derivative upon exposure to light. Additional examples of photoactivatable caging molecules that can be present in caged tamoxifen derivative molecules are described herein. In some embodiments, there is a linking group present between the tamoxifen derivative and the photoactivatable caging molecule. In some embodiments, the tamoxifen derivative and the photoactivatable caging molecule are joined by an ester, an ether, an amido group, a carbonate, a carbamate, or an acetal.

By the term "tissue-specific promoter sequence" is meant a nucleic acid sequence that is bound by a transcription factor and promotes the transcription of an operably linked gene within a specific tissue in a mammal Non-limiting examples of tissue-specific promoter sequences are described herein. Additional examples of tissue-specific promoter sequences are known in the art.

By the term "inducible promoter sequence" is meant a nucleic acid sequence that is bound by a transcription factor and promotes the transcription of an operably linked gene when the transcription factor is contacted with a chemical inducing agent (e.g., tetracycline). Non-limiting examples of inducible promoters and chemical inducing agents are described herein. Additional examples of inducible promoters and chemical inducing agents are known in the art.

By the term "ubiquitous promoter" is meant a nucleic acid sequence that is bound by a transcription factor and promotes transcription of an operably linked gene in a majority of the tissues present within a mammal (e.g., β-actin promoter). Non-limiting examples of ubiquitous promoters are described herein. Additional examples of ubiquitous promoters are known in the art.

By the term "recombinase" is meant an enzyme that recognizes a recombinase recognition sequence present within a double stranded DNA, cleaves the double stranded DNA within or near the recombinase recognition sequence, and ligates at least one of the severed ends of the double-stranded DNA to form a contiguous piece of DNA. In some embodiments, the activity of a recombinase results in the deletion of a nucleic acid sequence located between two different recombinase recognition sequences. In some embodiments, the activity of a recombinase results in the replacement of the sequence between two different recombinase recognition sequences with a different nucleic acid sequence (a different nucleic acid sequence that has a recombinase recognition sequence located at its 5' and 3' ends). Non-limiting examples of recombinases and recombinase recognition sequences are described herein. Additional examples of recombinases and recombinase recognition sequences are known in the art.

By the term "recombinant gene construct" is meant a heterologous artificial gene construct that is stably introduced into a chromosome of a eukaryotic (e.g., mammalian, plant, yeast, nematode, parasite, or reptile) cell. In some embodiments, the recombinant gene construct contains a sequence encoding an ER fusion protein (e.g., any of the ER fusion proteins described herein). In some embodiments, the recombinant gene construct contains a sequence encoding an ER fusion protein operatively linked to one or more promoter or enhancer sequences (e.g., an inducible, tissue-specific, or ubiquitous promoter). In some embodiments, the recombinant gene construct contains a nucleic acid sequence that contains at least one recombinase recognition sequence (e.g., any of the recombinase recognition sequences described herein or known in the art).

As is used throughout, the term "transgenic" refers to a eukaryotic (e.g., mammalian, plant, yeast, nematode, parasite, or reptile) cell in vitro or a non-human eukaryote (e.g., mammal) that contains at least one recombinant gene construct.

By the term "transcription repressor" is meant a protein that binds to a promoter sequence in DNA and mediates a decrease in the transcription of a nucleic acid sequence operatively linked to the promoter sequence.

By the term "transcription factor" or "transcription activator" is meant a protein that binds to a promoter sequence in DNA and mediates an increase in the transcription of a nucleic acid sequence operatively linked to the promoter sequence.

By the term "oncogene" is meant a polypeptide that contributes to the development of cancer in a mammal. In some embodiments, the oncogene results in a decreased function in an apoptotic signaling pathway in a mammalian cell. In some embodiments, the oncogene results in the deregulation of the cell cycle in a mammalian cell. A variety of different oncogenes are known in the art.

Other definitions appear in context throughout this disclosure. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION OF THE INVENTION

Figure 1:
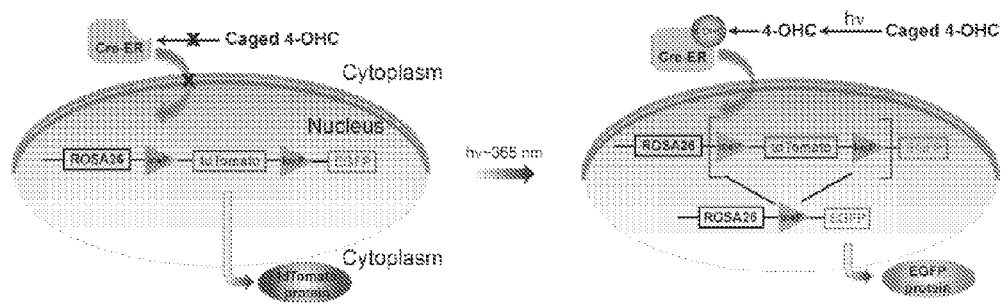
FIG. 1 is a schematic showing the photoactivation-dependent CreER/loxP system in the Rosa26CreER$^{T2}$; mT/mG reporter mice.

The invention is based, in part, on the discovery that photoactivatable caged tamoxifen and caged tamoxifen derivative molecules can be used to selectively and sensitively deliver tamoxifen or tamoxifen derivatives to cells following irradiation. Thus, provided herein are compositions containing these caged tamoxifen and caged tamoxifen derivative molecules, and methods of inducing nuclear translocation of an ER fusion protein in a eukaryotic (e.g., mammalian, plant, yeast, nematode, parasite, or reptile) cell and methods of inducing recombination in a eukaryotic (e.g., mammalian, plant, yeast, nematode, parasite, or reptile) cell that include contacting a eukaryotic cell with one of the caged tamoxifen or caged tamoxifen derivative molecules and irradiating the eukaryotic cell. Also provided are methods of treating breast cancer in a subject that include administering a photoactivatable caged tamoxifen or caged tamoxifen derivative molecule to a subject having breast cancer. Various, non-limiting features of each aspect of the invention are described below.

Compounds

Provided herein are caged tamoxifen and caged tamoxifen derivative molecules that are sensitive to light-induced degradation. Light exposure of the caged tamoxifen or caged tamoxifen derivative molecules triggers the release of the tamoxifen or tamoxifen derivative. Any of the caged tamoxifen or caged tamoxifen derivative molecules described herein can be used in any of the methods described herein.

A prior version of caged tamoxifen (4-hydrocyclofen conjugated with the photoactivatable 4,5-demethoxy-2-nitrophen methanol (DMNPM) group demonstrated spontaneous breakdown in the absence of appropriate light exposure. These results indicated that the DMNPM caging group or the DMNPM caged 4-hydroxycyclofen can be unstable in the absence of appropriate light exposure. In addition, the photocleavage of the DMNPM caged 4-hydroxycyclofen results in the generation of a reactive aldehyde group (shown in Schematic #1 below). This reactive aldehyde product may trigger unwanted side reactions with amine containing biomolecules in the cell. This process can lead to unwanted, detrimental chemical side reactions in the cell.

Schematic #1. Breakdown of DMNPN-caged 4-hydroxycyclofen

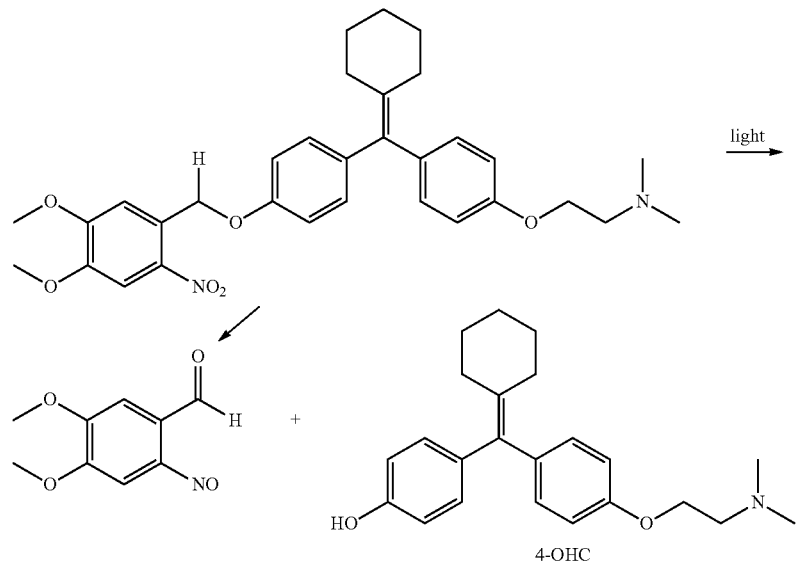

Provided herein are caged tamoxifen or caged tamoxifen derivative molecules that have improved stability in the absence of appropriate light exposure. In some embodiments, the caged tamoxifen or caged tamoxifen derivative molecules contain tamoxifen or a tamoxifen derivative (e.g., 4-hydroxycyclofen) conjugated to 1-(4,5-dimethoxy-2-nitrophenyl) ethanol (DMNPE). In some embodiments, the caged tamoxifen or caged tamoxifen derivative is conjugated to photoactivatable caging group selected from the group of: carboxy-2-nitrobenzyl (CNB); 4,5-dimethoxy-2-nitrobenzyl (DMNB); 2,2'-dinitrobenzhydryl (DNBH); 1-(2-nitrophenyl)ethyl (NPE); (4,4'-bis-{8-[4-nitro-3-(2-propyl)-styryl]}-3,3'-dimethoxybiphenyl (BNSMB); (2,7-bis-{4-nitro-8-[3-(2-propyl)-styryl]}-9,9-bis-[1-(3,6-dioxaheptyl)]-fluorene (BNSF); 4-carboxymethoxy-5,7-dinitroindolinyl (CDNI); 2-nitrobenzyl and 7-nitroindoline derivatives; coumarin-4-ylmethyl; 8-bromo-7-hydroxyquinoline derivatives; p-hydroxyphenacyl; and heavy metal. In some embodiments, the photoactivatable caging molecule is connected to the tamoxifen or tamoxifen derivative by an ester, an ether, an amido group, a carbonate, a carbamate, or an acetal.

In some embodiments, the tamoxifen derivative contains a modification to the triphenyl ethylene skeleton. Non-limiting examples of tamoxifen derivatives include 4-hydroxycyclofen and 4-hydroxytamoxifen. Additional non-limiting examples of tamoxifen derivatives are shown below (Schematic #2).

Schematic #2. Exemplary Tamoxifen Derivatives

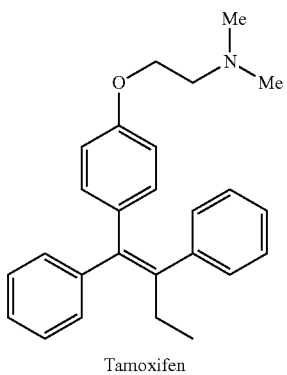

Tamoxifen

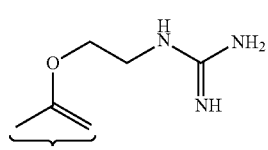
7

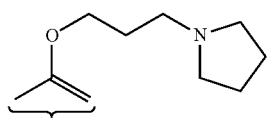
8

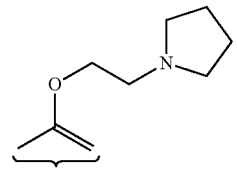
9

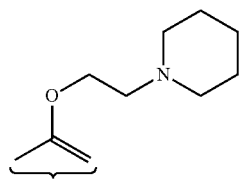
10

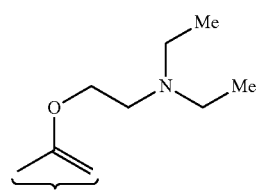
11

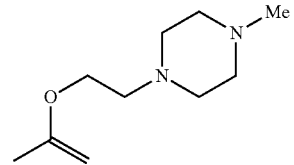
12

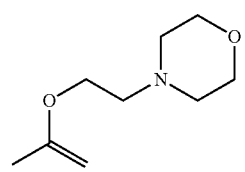
13

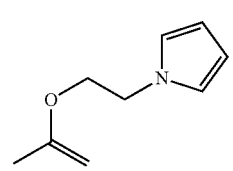
14

In some embodiments, the caged tamoxifen derivative molecule is 1-(4,5-dimethoxy-2-nitrophenyl) ethanol (DMNPE) caged 4-hydroxycyclofen (DMNPE-4-OHC). DMNPE-4-OHC did not appear to show any sign of breakdown prior to illumination (essentially inert in the dark). DMNPE-4-OHC can be decaged using a wavelength of light between 350 nm and 405 nm (see Example). The light-induced breakdown of DMNPE-4-OHC generates a ketone product (shown in Schematic #3 below), rather than a reactive aldehyde-containing product. The production of a ketone product reduces the possibility of any detrimental side reactions within a cell.

Schematic #3. Breakdown of DMNPE-4-OHC to Release 4-OHC
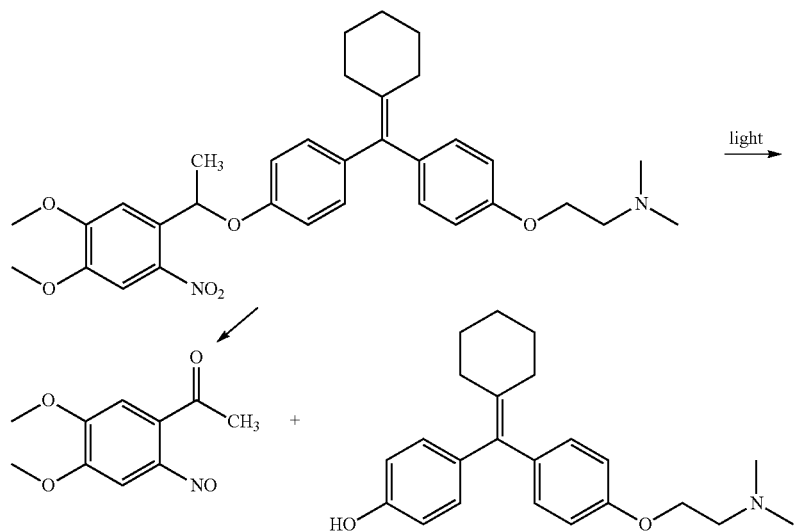
In some embodiments, the caged tamoxifen derivative is one of the structures shown in Schematic #4 below.
Schematic #4. Additional Exemplary DMNPE-Tamoxifen Derivatives
Caged Molecule A
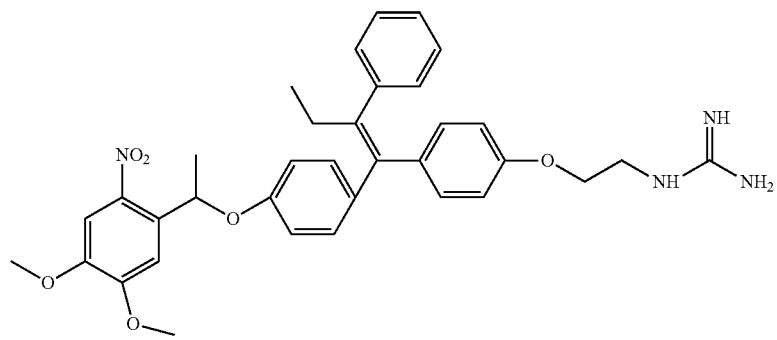
Caged Molecule B
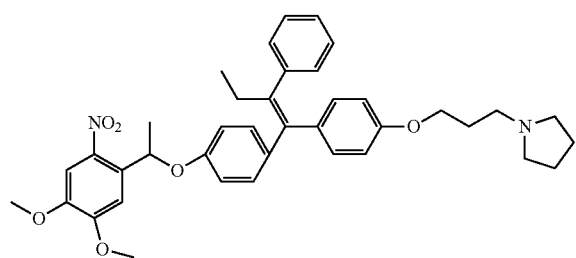
Caged Molecule C
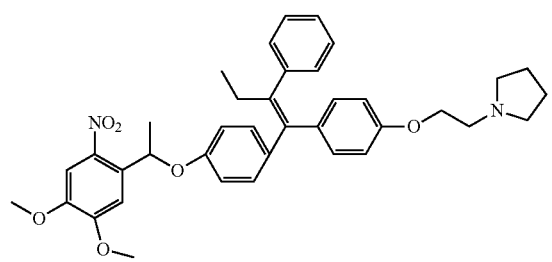
Caged Molecule D
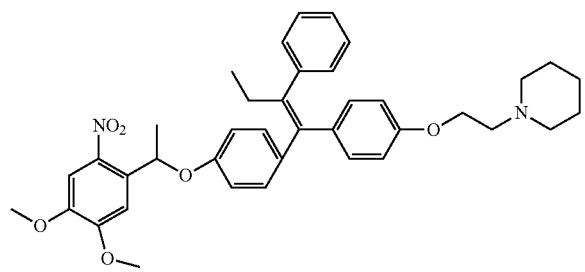
Caged Molecule E
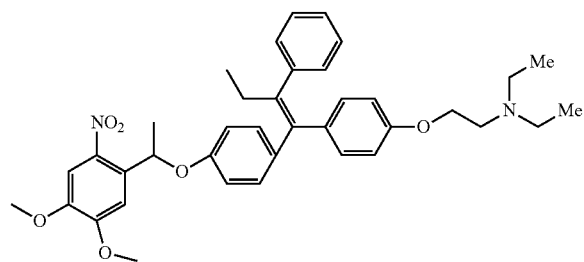

-continued

Caged Molecule F

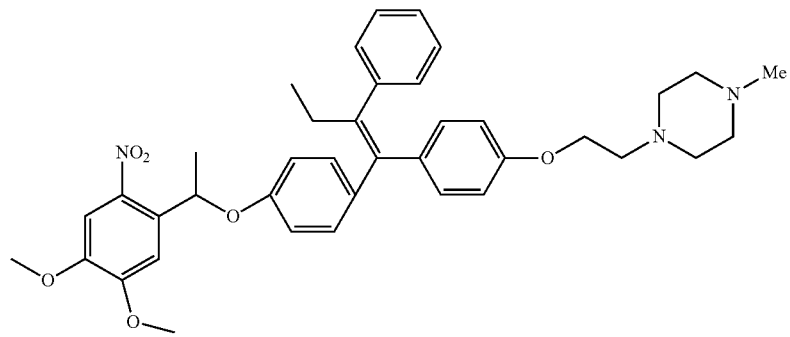

Caged Molecule G

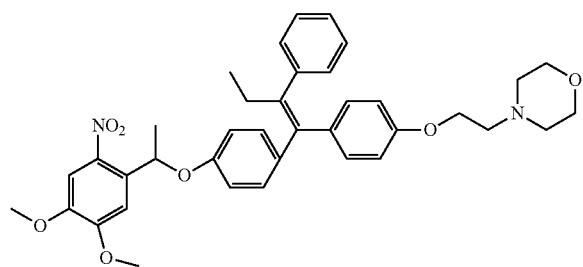

Caged Molecule H

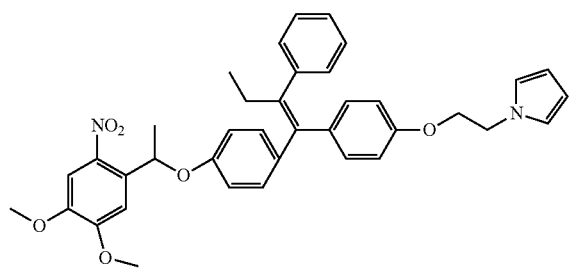

In some embodiments, the caged tamoxifen derivative is one of the three structures shown in Schematic #5 below.

Schematic #5. Additional Exemplary Caged Tamoxifen Derivatives

Caged Molecule I

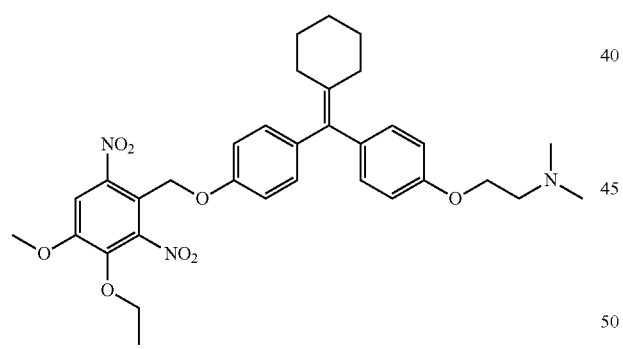

Caged Molecule II

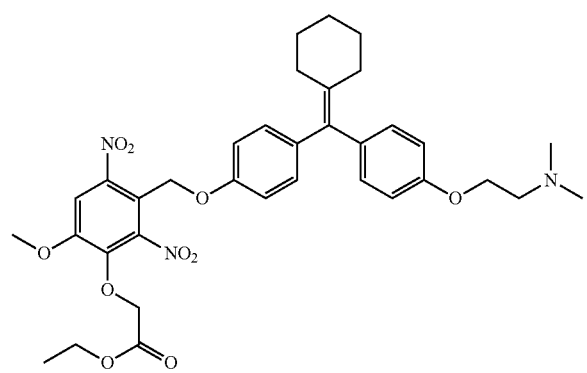

-continued

Caged Molecule III

Figure 17:
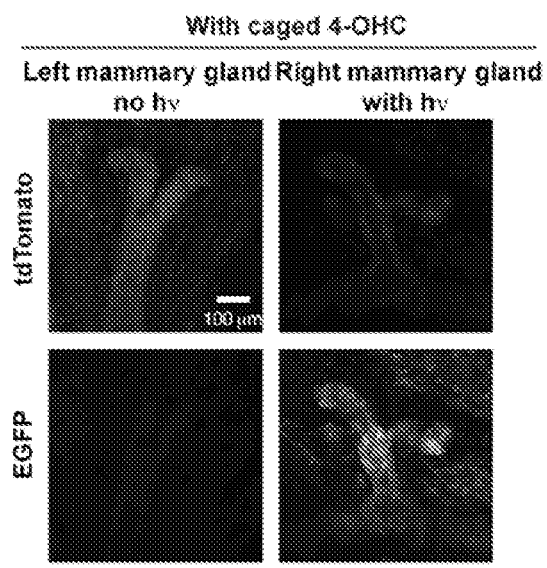
FIG. 17 is a set of four images of ex vivo mammary tissue from Rosa26CreER$^{T2}$; mT/mG female mice intraperitoneally injected with caged 4-OHC and exposed (right panels) or unexposed (left panels) to 365 nm light. The mammary tissue was imaged with an IV-110 epifluorescent imager. The illuminated mammary gland tissues injected with caged 4-OHC expressed EGFP.

Caged Molecules I, II, and III (shown in Schematic #5) were tested in cell culture experiments and were able to induce nuclear translocation of an ER fusion protein in vitro (see, FIG. 17). Caged Molecule III (shown in Schematic #5) is a two-photon activatable caged tamoxifen derivative. Activation using a two-photon light source is particularly beneficial for in vivo study due to its ability to allow deep tissue penetration and low tissue damaging effect. A two-photon light source emits wavelengths that are greater than 600 nm (e.g., emits a wavelength that is between 700 nm and 800 nm, between 700 nm and 900 nm, between 650 nm and 850 nm, between 500 nm and 800 nm, or between 600 nm and 900 nm). In some embodiments where the nuclear translocation of an ER fusion protein within an internal organ is desired, a mammal is administered a composition containing Caged Molecule III (shown in Schematic #5 above).

In some embodiments, the caged tamoxifen derivative is DMNPE-conjugated 4-hydroxy tamoxifen (shown in Schematic #6 below). 4-hydroxy tamoxifen is the active metabolite form of tamoxifen. As described below, the DMNPE-conjugated 4-hydroxy tamoxifen can be used as a prodrug for light-induced localized treatment of breast cancer in a subject.

Schematic #6. DMNPE-conjugated 4-hydroxy tamoxifen

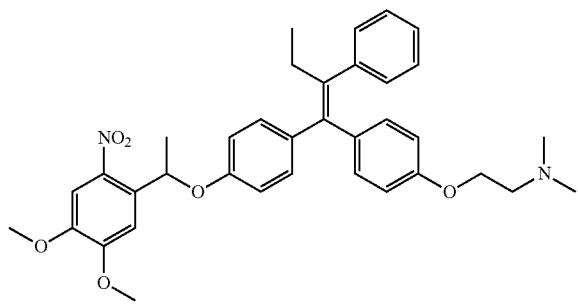

Synthetic methods for conjugating tamoxifen or a tamoxifen derivative (e.g., any of the tamoxifen derivatives described herein) to a photoactivatable caging molecule (e.g., any of the caging molecules described herein) are known in the art. For example, DMNPE can be conjugated to a tamoxifen derivative (e.g., 4-hydroxycyclofen) using Mitsonobu coupling conditions (see, e.g., the method described in the Example). In some embodiments, the tamoxifen or tamoxifen derivative can be conjugated to a bromo derivative of the photoactivatable-caged molecule (e.g., DMNPE) via a nucleophilic substitution reaction. After the synthesis, the caged tamoxifen or caged tamoxifen derivative molecule can be purified, e.g., using a $SiO_2$ (see, e.g., the method described in the Example). In some embodiments, the caged tamoxifen or caged tamoxifen derivative molecule can be at least 80% (e.g., at least 85%, 90%, 95%, or 99%) pure by weight.

Compositions and Kits

Provided herein are compositions containing at least one of any of the caged tamoxifen molecules or caged tamoxifen derivative molecules described herein. In some embodiments, the composition contains at least 80% (e.g., at least 85%, 90%, 95%, or 99%) of the caged tamoxifen or the caged tamoxifen derivative molecule by weight. In some embodiments, the composition contains a pharmaceutically acceptable excipient or buffer (e.g., saline, DMSO, PEG400, an acetate buffer, VitE-TPGS, ethanol, Solutol, cremophor, Tween, and mixtures thereof). In some embodiments, the compositions are formulated using a combination of ethanol, a polyethylene glycol, Tween, and Solutol. In some embodiments, the compositions are formulated in 10% N,N-dimethylacetamide (DMAC) and 10% Solutol in saline.

In some embodiments, the compositions are formulated as a liquid for systemic administration. In some embodiments, the compositions are formulated for intraarterial, intravenous, intraperitoneal, intrathecal, ocular, nasal, intramuscular, intraductal, or subcutaneous administration.

In some embodiments, the compositions are formulated as a solid. In some embodiments, the compositions are formulated for oral or topical (e.g., transdermal) administration. In some embodiments, the compositions are formulated as a suppository.

In some embodiments, the compositions are encapsulated in nanomaterials for targeted delivery (e.g., encapsulated in a nanomaterial having one or more tissue- or cell-targeting molecules on its surface). In some embodiments, the compositions are formulated as an emulsion or as a liposome-containing composition. In some embodiments, the compositions can contain dimers, multimers, or polymers of any of the caged tamoxifen or caged tamoxifen derivative molecules described herein. In some embodiments, the caged tamoxifen or caged tamoxifen derivative molecules are formulated for sustained release (e.g., formulated in a biodegradable polymers or in nanoparticles). In some embodiments, the compositions are formulated in an implantable device that allows for sustained release of the caged tamoxifen or caged tamoxifen derivative molecules.

Pharmaceutical compositions are formulated to be compatible with their intended route of administration or the intended target tissue or cell, e.g., systemic or local administration. In some embodiments, the compositions are formulated for oral, intravenous, intradermal, subcutaneous, transmucosal (e.g., nasal sprays are formulated for inhalation), or transdermal (e.g., topical ointments, salves, gels, patches, or creams as generally known in the art) administration. The compositions can include a sterile diluent (e.g., sterile water or saline), a fixed oil, polyethylene glycol, glycerine, propylene glycol, or other synthetic solvents; antibacterial or antifungal agents, such as benzyl alcohol or methyl parabens, chlorobutanol, phenol, ascorbic acid, thimerosal, and the like; antioxidants, such as ascorbic acid or sodium bisulfate; chelating agents, such as ethylenediaminetetraacetic acid; buffers such as acetates, citrates, or phosphates; and isotonic agents, such as sugars (e.g., dextrose), polyalcohols (e.g., manitol or sorbitol), or salts (e.g., sodium chloride). Liposomal suspensions can also be used as pharmaceutically acceptable carriers (see, e.g., U.S. Pat. No. 4,522,811; herein incorporated by reference). Preparations of the compositions can be formulated and enclosed in ampules, disposable syringes, or multiple dose vials that prevent exposure of the caged tamoxifen or caged tamoxifen derivative molecules to light. Where required (as in, for example, injectable formulations), proper fluidity can be maintained by, for example, the use of a coating such as lecithin, or a surfactant. Absorption of the caged tamoxifen or caged tamoxifen derivative molecules can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Where oral administration is intended, the agent can be included in pills, capsules, troches and the like, and can contain any of the following ingredients, or compounds of a similar nature: a binder, such as microcrystalline cellulose, gum tragacanth, or gelatin; an excipient, such as starch or lactose; a disintegrating agent, such as alginic acid, Primogel, or corn starch; a lubricant, such as magnesium stearate; a glidant, such as colloidal silicon dioxide; a sweetening agent, such as sucrose or saccharin; or a flavoring agent, such as peppermint, methyl salicylate, or orange flavoring.

The compositions described herein can be formulated for ocular or parenteral (e.g., oral) administration in dosage unit form (i.e., physically discrete units containing a predetermined quantity of active compound for ease of administration and uniformity of dosage). Toxicity and therapeutic efficacy of compounds can be determined by standard pharmaceutical procedures in cell cultures or experimental animals. One can, for example, determine the LD50 (the dose lethal to 50% of the population) and the ED50 (the dose therapeutically effective in 50% of the population), the therapeutic index being the ratio of LD50:ED50. Agents that exhibit high therapeutic indices are preferred. Where an agent exhibits an undesirable side effect, care should be taken to target that agent to the site of the affected or targeted tissue (the aim being to minimize potential damage to unaffected cells and, thereby, reduce side effects). Toxicity and therapeutic efficacy can be determined by other standard pharmaceutical procedures.

In some embodiments, the composition containing a caged tamoxifen or caged tamoxifen derivative molecule is formulated in a single dosage form (e.g., a single dosage form containing between 1 mg to 500 mg, between 1 mg and 400 mg, between 1 mg and 300 mg, between 1 mg and 250 mg, between 1 mg and 200 mg, between 1 mg and 100 mg, and between 1 mg and 50 mg of the caged tamoxifen or caged tamoxifen derivative molecule).

In some embodiments, the compositions contain at least one caged tamoxifen molecule or at least one caged tamoxifen derivative molecule and one or more additional breast cancer therapeutics (e.g., any of the breast cancer therapeutics described herein).

Also provided herein are kits that contain at least one dose of any of the compositions described herein. In some embodiments, the kits can further include an item for use in administering a composition (e.g., any of the compositions described herein) to the subject (e.g., a syringe, e.g., a pre-filled syringe). In some embodiments, the kits contain one or more doses (e.g., at least two, three, four, five, six, seven, eight, nine, ten, eleven, twelve, thirteen, fourteen, twenty, thirty, or forty doses) (e.g., oral doses) of any of the compositions described herein. In some embodiments, the kit further contains instructions for administering the composition (or a dose of the composition) to a mammal (e.g., a non-human transgenic mammal or a human having breast cancer). In some embodiments, the kits contain a composition containing at least one of the caged tamoxifen molecules or at least one of the caged tamoxifen derivative molecules, and a composition containing at least one additional breast cancer therapeutic (e.g., any of the additional breast cancer therapeutics described herein). In some embodiments, the kit further contains instructions for performing any of the methods described herein In some embodiments, the kits can further contain a light source (e.g., any of the light sources described herein, e.g., a hand-held light source or a light source that can be used in an endoscopic or orthoscopic procedure). In some embodiments, the kits contain a two-photon light source (e.g., a hand-held two photon light source). In some embodiments, a light source emits a wavelength of light that is between 700 nm and 800 nm, between 700 nm and 900 nm, between 650 nm and 850 nm, between 500 nm and 800 nm, or between 600 nm and 900 nm. In some embodiments, the light source emits light at a wavelength of approximately 730 nm.

Light Sources

Light sources that emit light between 200 nm and 900 nm (e.g., between 300 nm and 700 nm, between 300 nm and 600 nm, between 300 nm and 500 nm, between 350 nm and 410 nm, between 200 nm and 700 nm, and between 700 nm and 900 nm) that can be used to breakdown the caged tamoxifen or caged tamoxifen derivative molecules (e.g., any of the caged tamoxifen or caged tamoxifen derivative molecules described herein). In some embodiments, the light source emits a wavelength of between 700 nm and 800 nm, between 700 nm and 900 nm, between 650 nm and 850 nm, between 500 nm and 800 nm, or between 600 nm and 900 nm. In some embodiments, a light source that emits light of 350 nm to 410 nm is used to breakdown DMNPE-caged 4-hydroxy-cyclofen.

In some embodiments, the light source can be directed to a particular tissue or cell that is expressing the ER fusion protein (e.g., any of the ER fusion proteins described herein) and that has been contacted with any of the caged tamoxifen or caged tamoxifen derivative molecules described herein. In some embodiments, the light source is used to irradiate an animal containing a cell containing the ER fusion protein that has been contacted with any of the caged tamoxifen or caged tamoxifen derivative molecules described herein. In some embodiments, the light source is a hand-held device. In some embodiments, the light source is placed at the end of an endoscope or orthoscopic device. In some embodiments, the light source is inserted into a tissue in the body through the use of a catheter. In some embodiments, the light source is a two-photon light source.

ER Fusion Proteins

Estrogen receptor (ER)-fusion proteins as described herein are proteins that contain a mammalian estrogen receptor ligand binding domain and an additional polypeptide sequence (a fusion partner polypeptide). In some embodiments, the ER-fusion protein contains a human estrogen receptor ligand binding domain. In some embodiments, the mammalian (e.g., human) estrogen receptor ligand binding domain is located at the N-terminus of the ER-fusion protein or is located N-terminal to the additional polypeptide sequence (fusion partner polypeptide). In some embodiments, the mammalian (e.g., human) estrogen receptor ligand binding domain is located at the C-terminus of the ER fusion protein or is located C-terminal to the additional polypeptide sequence (fusion partner polypeptide).

Mammalian Estrogen Receptor Ligand Binding Domains

In some embodiments, the mammalian estrogen receptor ligand binding domain contains a contiguous sequence that is at least 80% (e.g., at least 85%, 90%, 95%, 96%, 97%, 98%, 99%, or 100%) identical to a contiguous sequence present in a human estrogen ligand binding domain, and has the ability to bind to tamoxifen or a tamoxifen derivative (e.g., any of the tamoxifen derivatives described herein). In some embodiments, the mammalian estrogen receptor ligand binding domain contains a sequence that is at least 80% (e.g., at least 85%, 90%, 95%, 96%, 97%, 98%, 99%, or 100%) identical to a contiguous sequence present between amino acids 310 to 547 of SEQ ID NO: 1 (underlined below). In some embodiments, amino acids 346, 351, 353, 387, 394, 521, 524 of SEQ ID NO: 1 are conserved (underlined and in bold below).

```
Human Estrogen Receptor Protein
                                                          (SEQ ID NO: 1)
   1 mtmtlhtkas gmallhqiqg neleplnrpq lkiplerplg evyldsskpa vynypegaay 61 efnaaaaana qvygqtglpy gpgseaaafg snglggfppl nsyspsplml lhpppqlspf 121 lqphgqqvpy ylenepsgyt vreagppafy rpnsdnrrqg grerlastnd kgsmamesak 181 etrycavcnd yasgyhygvw scegckaffk rsiqghndym cpatnqctid knrrkscqac 241 rlrkcyevgm mkggirkdrr ggrmlkhkrq rddgegrgev gsagdmraan lwpsplmikr
```

```
301 skknslalsl tadqmvsall daeppilyse ydptrpfsea smmglltnla drelvhminw 361 akrvpqfvdl tlhdqvhlle cawleilmiq lvwrsmehpq kllfapnlll drnqqkcveq 421 mveifdmlla tssrfrmmnl qgeefvclks iillnsqvyt flsstlksle ekdhihrvld 481 kitdtlihlm akaqltlqqq hqrlaqllli lshirhmsnk gmehlysmkc knvvplydll 541 lemldahrlh aptsrggasv eetdqshlat agstsshslq kyyitgeaeg fpatv
```

An exemplary cDNA encoding a human estrogen receptor protein is SEQ ID NO: 2.

Additional examples of human estrogen receptor ligand binding domains that can be used in the fusion proteins are described in Pfannkuche et al., *Biotechniques* 48:113-120, 2010; Andersson et al., *Transgenic Res.* 19:715-725, 2010; Maeda et al., *Bone* 46:472-478, 2010; Tumurbaatar et al., *J. Virol. Methods* 146:5-13, 2007; Dworniczak et al., *Nephron Exp. Nephrol.* 106:e11-e20, 2007; Weber et al., *Biol. Reprod.* 68:553-539, 2003; Hayashi et al., *Dev. Biol.* 244:305-318, 2002; Vallier et al., *Proc. Natl. Acad. Sci. U.S.A.* 98:2467-2472, 2001; Fuhrmann-Benzakein et al., *Nucleic Acids Res.* 28:E99, 2000; Indra et al., *Nucleic Acids Res.* 27:4324-4327, 1999; and Metzger et al., *Proc. Natl. Acad. Sci. U.S.A.* 92:6991-6995, 1995. These references describe Cre recombinase-human estrogen receptor ligand binding domain fusion proteins. Sequences encoding the human estrogen receptor ligand binding domain are described in these references, and these sequences can be isolated and used to form any of the ER fusion proteins described herein using molecular biology methods known in the art.

In some embodiments, the mammalian estrogen receptor ligand binding domain contains a contiguous sequence that is at least 80% (e.g., at least 85%, 90%, 95%, 96%, 97%, 98%, 99%, or 100%) identical to a contiguous sequence present in a mouse estrogen receptor ligand binding domain. In some embodiments, the mammalian estrogen receptor ligand binding domain contains a sequence that is at least 80% (e.g., at least 85%, 90%, 95%, 96%, 97%, 98%, 99%, or 100%) identical to a contiguous sequence present between amino acids 314 to 551 of SEQ ID NO: 3 (underlined below). In some embodiments, amino acids 350, 355, 357, 391, 398, 525, and 528 of SEQ ID NO: 3 are conserved (underlined and in bold below).

```
Mouse Estrogen Receptor Protein
                                                       (SEQ ID NO: 3)
  1 mtmtlhtkas gmallhqiqg neleplnrpq lkmpmeralg evyvdnskpt vfnypegaay 61 efnaaaaaaa aasapvygqs giaygpgsea aafsanslga fpqlnsysps plmllhpppq 121 lspflhphgq qvpyylenep sayavrdtgp pafyrsnsdn rrqngrerls ssnekgnmim 181 esaketryca vcndyasgyh ygvwscegck affkrsiqgh ndymcpatnq ctidknrrks 241 cqacrlrkcy evgmmkggir kdrrggrmlk hkrqrddleg rnemgasgdm raanlwpspl 301 vikhtkknsp alsltadqmv salldaeppm iyseydpsrp fseasmmqll tnladrelvh 361 minwakrvpq fqdlnlhdqv hllecawlei lmiqlvwrsm ehpqkllfap nllldrnqqk 421 cveqmveifd mllatssrfr mmnlqqeefv clksiillns qvytflsstl ksleekdhih 481 rvldkitdtl ihlmakaqlt lqqqhrrlaq lllilshirh msnkgmehly nmkcknvvpl 541 ydlllemlda hrlhapasrm gvppeepsqt qlattsstsa hslqtyyipp eaegfpnti
```

An exemplary cDNA encoding a mouse estrogen receptor protein is SEQ ID NO: 4.

In some embodiments, the mammalian estrogen receptor ligand binding domain contains a contiguous sequence that is at least 80% (e.g., at least 85%, 90%, 95%, 96%, 97%, 98%, 99%, or 100%) identical to a contiguous sequence present in a rat estrogen receptor ligand binding domain. In some embodiments, the mammalian estrogen receptor ligand binding domain contains a sequence that is at least 80% (e.g., at least 85%, 90%, 95%, 96%, 97%, 98%, 99%, or 100%) identical to a contiguous sequence present between amino acids 315 to 552 of SEQ ID NO: 5 (underlined below). In some embodiments, amino acids 351, 356, 358, 392, 399, 526, and 529 of SEQ ID NO: 5 are conserved (underlined and in bold below).

```
Rat Estrogen Receptor Protein
                                                       (SEQ ID NO: 5)
  1 mtmtlhtkas gmallhqiqg neleplnrpq lkmpmeralg evyvdnskpa vfnypegaay 61 efnaaaaaaa agasapvygq ssitygpgse aaafganslg afpqlnsysp splmllhppp
```

```
121 hvspflhphg hqvpyylene psayavrdtg ppafyrsnsd nrrqngrerl ssssekgnmi 181 mesaketryc avcndyasgy hygvwscegc kaffkrsiqg hndymcpatn qctidknrrk 241 scqacrlrkc yevgmmkggi rkdrrggrml khkrqrddle grnemgtsgd mraanlwpsp 301 lvikhtkkns palsltadqm vsalldaepp liyseydpsr pfseasmmql ltnladrelv 361 hminwakrvp gfgdlnlhdq vhllecawle ilmiglvwrs mehpgkllfa pnllldrnqg 421 kcveqmveif dmllatssrf rmmnlqqeef vclksiilln sqvytflsst lksleekdhi 481 hrvldkindt lihlmakagl tlqqqhrrla qlllilshir hmsnkgmehl ynmkcknvvp 541 lydlllemld ahrlhapasr mgvppeepsq sqltttssts ahslqtyyip peaegfpnti
```

An exemplary cDNA encoding a rat estrogen receptor protein is SEQ ID NO: 6.

The ability of an ER fusion protein to bind to tamoxifen or a tamoxifen derivative can be assessed directly using high performance liquid chromatograph-mass spectrometry (HPLC-MS) or circular dichroism (see, e.g., Nair et al., *J. Mol. Endocrinol.* 35:211-223, 2005). The ability of an ER fusion protein to bind tamoxifen or a tamoxifen derivative can also be assessed indirectly by the detection of the nuclear translocation of an ER fusion protein (e.g., detected by immunofluorescent microscopy or induced expression of a reporter transgene integrated within a chromosome of the cell) or the detection of an activity of the ER fusion protein within the nucleus of the cell. Exemplary methods for detecting tamoxifen- or tamoxifen derivative-induced nuclear translocation are described in the Examples. Methods for detecting the activity of an ER fusion protein within the nucleus of the cell depend on the specific activity of the ER fusion protein. Methods to detect the activity of an ER fusion protein within the nucleus of the cell are also known in the art.

Fusion Partner Polypeptides

ER fusion proteins can contain a fusion partner polypeptide from any source (e.g., a human, mouse, rat, bacterial, viral, or parasitic polypeptide sequence). In some embodiments, the fusion partner polypeptide contains a polypeptide sequence of a recombinase (e.g., a Cre recombinase from P1 phage, FLP from *S. cerevisiae*, λ integrase from lambda phage, gamma-delta resolvase from Tn1000 transposon, Tn3 resolvase from the Tn3 transposon, and φC31 integrase from φC31 phage) and the fusion protein has recombinase activity in a cell treated with tamoxifen or a tamoxifen derivative. Non-limiting exemplary sequences of Cre recombinase polypeptides that can be included in the ER fusion proteins, as well as exemplary ER fusion proteins containing a Cre recombinase polypeptide are described in Pfannkuche et al., *Biotechniques* 48:113-120, 2010; Andersson et al., *Transgenic Res.* 19:715-725, 2010; Maeda et al., *Bone* 46:472-478, 2010; Tumurbaatar et al., *J. Virol. Methods* 146:5-13, 2007; Dworniczak et al., *Nephron Exp. Nephrol.* 106:e11-e20, 2007; Weber et al., *Biol. Reprod.* 68:553-539, 2003; Hayashi et al., *Dev. Biol.* 244:305-318, 2002; Vallier et al., *Proc. Natl. Acad. Sci. U.S.A.* 98:2467-2472, 2001; Fuhrmann-Benzakein et al., *Nucleic Acids Res.* 28:E99, 2000; Indra et al., *Nucleic Acids Res.* 27:4324-4327, 1999; and Metzger et al., *Proc. Natl. Acad. Sci. U.S.A.* 92:6991-6995, 1995. Additional non-limiting polypeptide sequences of fusion partner polypeptides are listed in Table 1 below. Methods for detecting recombinase activity of a fusion protein in a cell treated with tamoxifen or a tamoxifen derivative are known in the art. Non-limiting exemplary methods for detecting recombinase activity of a fusion protein in a cell treated with tamoxifen or a tamoxifen derivative are described in the Example.

TABLE 1

| Exemplary Recombinase Fusion Partner Polypeptide Sequences | |
|---|---|
| Cre Recombinase | NCBI Accession No. AFA52013.1; nucleotides 2590 to 3621 of NCBI Accession No. JN798465.1 |
| Flp Recombinase | NCBI Accession No. AAT08996.1; nucleotides 6054 to 7325 of NCBI Accession No. AY597273.1 |
| Lambda Integrase | NCBI Accession No. ADW76527.1; nucleotides 108705 to 109829 of NCBI Accession No. CP002506.1 |
| Gamma Delta Resolvase | NCBI Accession No. P03012.1 |
| Tn3 Resolvase | NCBI Accession No. AEZ43735.1; nucleotides 1829 to 2386 of NCBI Accession No. CP003112.1 |
| φC31 Integrase | NCBI Accession No. CAI94541.1; nucleotides 5011 to 6852 of NCBI Accession No. AJ937361.1 |

In some embodiments, the fusion partner polypeptide contains a polypeptide sequence of a transcription factor (e.g., a transcription factor that plays a role in cellular differentiation) and the fusion protein is capable of inducing gene transcription in a cell treated with tamoxifen or a tamoxifen derivative. In some embodiments, the fusion partner polypeptide contains a polypeptide sequence of a transcription repressor (e.g., a transcription repressor that plays a role in cellular differentiation) and the fusion protein is capable of inhibiting gene transcription in a cell treated with tamoxifen or a tamoxifen derivative. In some embodiments, the fusion partner polypeptide contains a polypeptide sequence of a histone deacetylase and the fusion protein has histone deacetylase activity in a cell treated with tamoxifen or a tamoxifen derivative. In some embodiments, the fusion partner polypeptide contains a polypeptide sequence of an O-6-methylguanine-DNA methyltransferase and the fusion protein has O-6-methylguanine-DNA methyltransferase activity in a cell treated with tamoxifen or a tamoxifen derivative. In some embodiments, the fusion partner polypeptide contains a polypeptide sequence of a telomerase and the fusion protein has telomerase activity in a cell treated with tamoxifen or a tamoxifen derivative. Non-limiting exemplary sequences of histone acetyltransferase, histone deactyltransferase, O-6-methylguanine-DNA methyltransferase, and telomerase that can be present in an ER fusion protein are listed in Table 2 below. Methods for detecting gene transcription, histone deacetylase activity, histone acetyltransferase activity, O-6-methylguanine-DNA methyltransferase activity, and telomerase activity are known in the art.

TABLE 2

Exemplary Fusion Partner Polypeptides

| | |
|---|---|
| Histone Acetyltransferase | NCBI Accession Nos. AAD42348.1 and AF140360.1 |
| Histone Deacetylase | NCBI Accession Nos. AAQ18232.1 and AY302468.1 |
| O-6-Methylguanine-DNA Methyltransferase | NCBI Accession Nos. AAA59594.1 and M60761.1 |
| Telomerase | NCBI Accession Nos. NP_937983.2, NM_198253.2, NP_001180305.1, and NM_001193376.1 |

In some embodiments, the fusion partner polypeptide contains a polypeptide sequence of a viral protein (e.g., an adenoviral, lentiviral, or a retroviral protein). In some embodiments, the fusion partner polypeptide contains a polypeptide sequence from a pathogenic bacterium or a parasite. In some embodiments, the fusion partner polypeptide contains a polypeptide sequence of an oncogene (e.g., a human, mouse, rat, or monkey oncogene). Additional sequences of fusion partner polypeptides are described in the examples and are known in the art.

In some embodiments, the ER fusion proteins can contain a polypeptide sequence of an additional reporter protein (e.g., a fluorescent protein such as green fluorescent protein or yellow fluorescent protein, or an enzyme capable of producing a colored product (e.g., β-galactosidase) or an additional epitope (e.g., a His-tag).

Promoters

In some embodiments, a nucleic acid encoding the ER fusion protein (e.g., any of the ER fusion proteins described herein) is stably integrated into a chromosome in the nucleus of a eukaryotic (e.g., mammalian, plant, yeast, nematode, parasite, or reptile) cell. In some embodiments, a nucleic acid encoding the ER fusion protein is introduced into a chromosome of the eukaryotic (e.g., mammalian, plant, yeast, nematode, parasite, or reptile) cell using a recombinant virus (e.g., a recombinant adenovirus, lentivirus, or retrovirus). In some embodiments, a nucleic acid encoding the ER fusion protein is introduced into an embryo or blastocyst of non-human mammal to produce a transgenic mammal.

In some embodiments, a nucleic acid encoding the ER fusion protein (e.g., any of the ER fusion proteins described herein) is located in an expression plasmid or an artificial mammalian chromosome (e.g., a human artificial chromosome), and the expression plasmid or artificial mammalian chromosome is introduced into a mammalian cell (e.g., a mammalian embryo or blastocyst). In some embodiments, the eukaryotic cell is a yeast cell and a yeast artificial chromosome is introduced into the yeast cell. In some embodiments, the expression plasmid is introduced into the eukaryotic cell by electroporation or lipofection. In some embodiments, the artificial chromosome is introduced into the eukaryotic cell by microinjection or cell fusion (e.g., fusion of a target cell (e.g., an embryo) with a cell (e.g., a fetal fibroblast) containing a mammalian artificial chromosome). A variety of different eukaryotic (e.g., mammalian) expression plasmids and mammalian artificial chromosomes are known in the art. A variety of different molecular biology methods for introducing an expression plasmid or a mammalian artificial chromosome into a eukaryotic cell are also known in the art.

In some embodiments, one or more promoter or enhancer sequences can be operatively linked (e.g., upstream) to the sequence encoding the ER fusion protein. In some embodiments, the one or more promoter sequences can be a tissue-specific promoter, an inducible e promoter, or a ubiquitous (e.g., strong ubiquitous) promoter. Non-limiting examples of tissue-specific promoters include B29 promoter (B-cell expression), CD14 promoter (monocyte expression), CD43 promoter (leukocyte and platelet expression), CD45 promoter (haematopoietic cell expression), CD68 promoter (macrophage expression), desmin promoter (muscle cell expression), elastase-1 promoter (pancreatic acinar cell expression), endoglin promoter (endothelial cell expression), fibronectin promoter (differentiating cell expression), Flt-1 promoter (endothelial cell expression), GFAP promoter (astrocyte expression), GPIIB promoter (megakaryocyte expression), ICAM-2 promoter (endothelial cell expression), INF-β promoter (hematopoietic cell expression), Mb promoter (muscle cell expression), NphsI promoter (podocyte expression), OG-2 promoter (osteoblast expression), SP-B promoter (lung cell expression), SYN1 promoter (neuron expression), WASP promoter (hematopoietic cell expression), SV40/bAlb promoter (liver cell expression), and NSE/Ru5' promoter (mature neuron expression) (these promoter sequences are available in commercially available vectors, e.g., expression vectors available from InvivoGen). In some embodiments, an aromatase promoter is used to drive expression of the ER fusion protein in breast tissue (see, e.g., Khan et al., Reprod. Biol. Endocrinol. 9:91, 2011). In some embodiments, a carbonic anhydrase I promoter/enhancer is used to express the ER fusion protein in colon tissue (see, e.g., Xue et al., Mol. Cancer Res. 8:1095, 2010). In some embodiments, a keratin 14 promoter is used to express the ER fusion protein in skin tissue (see, e.g., Vandermeulen et al., Vaccine 27:4272-4277, 2009). Additional examples of tissue-specific promoter sequences are known in the art.

In some embodiments, the nucleic acid encoding the ER fusion protein is operatively linked (e.g., upstream) to an inducible promoter sequence and the cell is further contacted with a chemical inducing agent. Non-limiting examples of inducible promoter sequences include tetracycline-regulated promoters (see, e.g., the T-Rex™ system from Life Technologies), doxycycline-inducible promoters (see, e.g., Qin et al., PLoS ONE 5:e10611, 2010), RU486-inducible promoters (see, e.g., U.S. Patent Application Publication No. 2009/0293139), and polyinosinic:polycytidylic acid (Poly(I:C))-inducible promoters (Tomita et al., Mol. Endocrinol. 14:1674-1681, 2000). Additional inducible promoter sequences and chemical inducing agents are known in the art.

In some embodiments, the nucleic acid encoding the ER fusion protein is operatively linked (e.g., upstream) to a ubiquitous (e.g., a strong ubiquitous) promoter sequence. Non-limiting examples of ubiquitous promoters include β-actin promoter, CMV promoter, SV40 promoter, UBC promoter, EF1A promoter, PGK promoter, and CAGG promoter (see, e.g., Qin et al., PLoS One 5:e10611, 2010). One or more of the promoter sequences described herein can be operatively linked to a nucleic acid encoding an ER fusion protein using molecular biology methods known in the art.

Methods of Inducing Nuclear Translocation

Provided herein are methods of optically inducing nuclear translocation of a fusion protein containing a mammalian estrogen receptor ligand binding domain (e.g., a human estrogen receptor ligand binding domain) in a eukaryotic (e.g., mammalian, plant, yeast, nematode, parasite, or reptile) cell. These methods include providing a eukaryotic ((e.g., mammalian, plant, yeast, nematode, parasite, or reptile) cell that contains a fusion protein containing a mammalian (e.g., human) estrogen receptor ligand binding domain, contacting the cell with any of the compositions described herein; and irradiating the cell with a wavelength of light between of between 200 nm and 900 nm (e.g., between 350 nm to 410 nm, between 200 nm and 700 nm, and between 700 nm and 900 nm) for a period of time sufficient to stimulate release of tamoxifen or a tamoxifen derivative from the composition, where the released tamoxifen or tamoxifen derivative induces the nuclear translocation of the fusion protein. In some embodiments, the fusion protein is any of the fusion proteins (ER fusion proteins) described herein.

The nuclear translocation of a fusion protein can be detected using immunofluorescence using antibodies that bind specifically to either the mammalian estrogen receptor ligand binding domain or the fusion partner polypeptide. The nuclear translocation of the fusion protein can also be assessed by detecting the activity of the fusion protein in the nucleus of the cell (e.g., transcription factor activity, transcription repressor activity, telomerase activity, oncogene activity, histone deacetylase activity, histone acetyltransferase activity, or O-6-methylguanine DNA methyltransferase activity in the nucleus of the cell). In some embodiments, the fusion protein can further contain a detectable reporter protein (e.g., a green fluorescent protein or yellow fluorescent protein) that can be used to detect the presence of the fusion protein in the nucleus of the cell.

In some embodiments, the eukaryotic (e.g., mammalian, plant, yeast, nematode, parasite, or reptile) cell contains a nucleic acid encoding the fusion protein. In some embodiments, the nucleic acid encoding the fusion protein is stably integrated in a chromosome within the nucleus of the eukaryotic (e.g., mammalian, plant, yeast, nematode, parasite, or reptile) cell. In some embodiments, the nucleic acid encoding the fusion protein is located in an expression plasmid or a mammalian artificial chromosome (e.g., a human artificial chromosome). In some embodiments, the nucleic acid encoding the fusion protein is operably linked to one or more promoter or enhancer sequences. In some embodiments, the nucleic acid is operatively linked to a inducible promoter (e.g., any of the inducible promoters described herein or known in the art) and the cell is further contacted with a chemical inducing agent (e.g., any of the chemical inducing agents described herein or known in the art) (e.g., prior to contacting with the caged tamoxifen or caged tamoxifen derivative molecule, prior to contacting with the caged tamoxifen or caged tamoxifen derivative molecule and prior to irradiation, or after contacting with the caged tamoxifen or caged tamoxifen derivative molecule and after irradiation). In some embodiments, the nucleic acid encoding the fusion protein is operatively linked to a tissue-specific promoter (e.g., any of the tissue-specific promoters described herein or known in the art). In some embodiments, the nucleic acid encoding the fusion protein is operatively linked to a ubiquitous promoter (e.g., any of the ubiquitous promoters described herein or known in the art).

In some embodiments, the eukaryotic (e.g., mammalian, plant, yeast, nematode, parasite, or reptile) cell is present in vitro or ex vivo. In some embodiments, the eukaryotic (e.g., mammalian) cell is an epithelial cell, a lung cell, a kidney cell, an endothelial cell, a muscle cell, an adipose cell, a bone cell, a cartilage cell, or a neuron. In some embodiments, the eukaryotic (e.g., mammalian) cell is an undifferentiated cell or a stem cell (e.g., an embryonic stem cell) and the fusion protein contains a sequence of a transcription factor or a transcription repressor that induces cellular differentiation. In some embodiments, the eukaryotic (e.g., mammalian) cell is implanted into a mammal following the contacting with the caged tamoxifen or caged tamoxifen derivative molecule and irradiation.

In some embodiments, the cell is present in a mammal (e.g., a mouse or rat). In some embodiments, the cell is present in the breast tissue, skin, kidney, lung, colon, liver, pancreas, stomach, intestine, colon, muscle, mammary gland, ovary, testes, prostate, brain, spinal cord, peripheral nerve, and heart of the mammal. In some embodiments, the mammal is a child. In some embodiments, the mammal is an adult. In some embodiments, the mammal is an embryo or blastocyst.

In some embodiments, the composition is locally administered to a tissue containing the cell. In some embodiments, the composition is systemically administered (e.g., intravenous, intaarterial, intramuscular, intraperitoneal, subcutaneous, oral, transdermal, ocular, nasal, or intrathecal administration). In some embodiments, more than one dose of the composition is administered to the mammal before the cell is irradiated. In some embodiments, the cell can be contacted with a dose of the composition and then irradiated several times (e.g., one or more (e.g., at least two, three, four, or five) rounds of contacting and irradiating can be performed).

In some embodiments, a mammal is administered a dose of between 1 mg to 500 mg of the composition (e.g., between 1 mg to 400 mg, between 1 mg to 300 mg, between 1 mg and 250 mg, between 1 mg and 200 mg, between 1 mg and 150 mg, between 1 mg and 100 mg, between 1 mg and 50 mg, between 5 mg and 50 mg, and between 5 mg and 40 mg).

In some embodiments, the fusion protein contains a sequence of a recombinase (e.g., any of the recombinases described herein or known in the art), and the fusion protein has recombinase activity. In some embodiments, the fusion protein contains a sequence of a transcription factor, and the transcription factor is capable of promoting gene transcription in the nucleus of the cell. In some embodiments, the fusion protein promotes gene transcription of a gene that is present in a recombinant gene construct that is stably integrated in a chromosome present in the nucleus of the cell. In some embodiments, the fusion protein promotes transcription of an endogenous gene. Methods of determining the ability of a fusion protein to promote gene transcription are known in the art (e.g., reverse-transcriptase real-time polymerase chain reaction (PCR)).

In some embodiments, the fusion protein contains a sequence of a transcription repressor, and the fusion protein is capable of repressing gene transcription in the nucleus of the cell. In some embodiments, the fusion protein represses gene transcription of a gene that is present in a recombinant gene construct that is stably integrated in a chromosome present in the nucleus of the cell. In some embodiments, the fusion protein represses gene transcription of an endogenous gene. Methods of determining the ability of a fusion protein to repress gene transcription are known in the art (e.g., reverse transcriptase real-time PCR).

In some embodiments, the fusion protein contains a sequence of a histone deacetylase, a histone acetyltransferase, or an O-6-methylguanine DNA methyltransferase, and the fusion protein has histone deacetylase, histone acetyltransferase, or O-6-methylguanine DNA methyltransferase activity, respectively. In some embodiments, the fusion protein contains a sequence of a telomerase, and the fusion protein has telomerase activity. Methods for determining the histone deacetylase, histone acetyltransferase, O-6-methylguanine DNA methyltransferase, or telomerase activity are known in the art.

In some embodiments, the fusion protein contains a sequence of an oncogene.

In some embodiments, the cell is irradiated for a period of at least 1 minute (e.g., at least 5, 10, 15, 20, 30, 40, 50, or 60 minutes). In some embodiments, the cell is illuminated for a maximum of 15, 20, 25, 30, 35, 40, 45, 50, 55, or 60 minutes. In some embodiments, the cell is illuminated using any of the light sources described herein (e.g., a hand-held light source). In some embodiments, the contacting and the irradiating occur within 24 hours of each other (e.g., within 20, 16, 12, 10, 8, 6, 4, 3, 2, or 1 hour of each other).

In some embodiments of all of these methods, the composition contains DMNPE-conjugated 4-hydroxycyclofen and the cell is irradiated with 350 nm to 410 nm light.

In some embodiments of all of these methods, the cell is irradiated with light of between 700 nm and 800 nm, between 700 nm and 900 nm, between 650 nm and 850 nm, between 500 nm and 800 nm, or between 600 nm and 900 nm.

Methods of Inducing Recombination

Also provided are methods of optically inducing recombination in a eukaryotic (e.g., mammalian, plant, yeast, nematode, parasite, or reptile) cell. These methods include: providing a eukaryotic (e.g., mammalian, plant, yeast, nematode, parasite, or reptile) cell that contains (i) a nucleic acid encoding a fusion protein containing a sequence of a recombinase and a sequence of a human estrogen receptor ligand binding domain, where the fusion protein has recombinase activity, and (ii) a recombinase recognition sequence that is specifically recognized by the fusion protein, where both the nucleic acid encoding the fusion protein and the recombinase recognition sequence are integrated into a chromosome within the nucleus of the cell; contacting the cell with any of the compositions described herein; and irradiating the cell with a wavelength of light between 200 nm to 900 nm (e.g., between 350 nm to 410 nm, between 200 nm and 700 nm, and between 700 nm and 900 nm) for a period of time sufficient to stimulate release of tamoxifen or a tamoxifen derivative from the composition, where the tamoxifen or tamoxifen derivative stimulates the nuclear translocation of the fusion protein and the fusion protein stimulates recombination at the recombinase recognition sequence. In some embodiments, the cell is irradiated with light between 700 nm and 800 nm, between 700 nm and 900 nm, between 650 nm and 850 nm, between 500 nm and 800 nm, or between 600 nm and 900 nm.

In some embodiments, the nucleic acid encodes a fusion protein containing a sequence of any of the recombinases described herein (e.g., a Cre recombinase). As is known in the art, each recombinase recognizes a unique recombinase recognition sequence. For example, Cre recombinase recognizes a 34-base pair loxP recombinase recognition sequence.

In some embodiments, the nucleic acid encoding the fusion protein is operably linked to one or more promoter or enhancer sequences. In some embodiments, the nucleic acid is operatively linked to a inducible promoter (e.g., any of the inducible promoters described herein or known in the art) and the cell is further contacted with a chemical inducing agent (e.g., any of the chemical inducing agents described herein or known in the art) (e.g., prior to contacting with the caged tamoxifen or caged tamoxifen derivative, prior to contacting with the caged tamoxifen or caged tamoxifen derivative and prior to irradiation, or after contacting with the caged tamoxifen or caged tamoxifen derivative and after irradiation). In some embodiments, the nucleic acid encoding the fusion protein is operatively linked to a tissue-specific promoter (e.g., any of the tissue-specific promoters described herein or known in the art). In some embodiments, the nucleic acid encoding the fusion protein is operatively linked to a ubiquitous promoter (e.g., any of the ubiquitous promoters described herein or known in the art).

In some embodiments, the nucleic acid encoding the fusion protein and the recombinase recognition sequence are located on different chromosomes in the nucleus of the cell. In some embodiments, the recombination results in a decrease in the expression of a transgene located between two recombinase recognition sequences in the chromosome. In some embodiments, the recombination results in the replacement of a sequence between two recombinase recognition sequences with a new transgenic sequence. In some embodiments, the recombination results in the increase in the proximity of a promoter or enhancer sequence to a transgene, wherein the recombination results in increased expression of the transgene. In some embodiments, the recombination results in the increase in the proximity of a repressor sequence or heterochromatin to a transgene, wherein the recombination results in decreased expression of the transgene.

In some embodiments, the removal of a sequence present between two recombinase recognition sequences results in an increase in the expression of a proximal transgene or proximal homologous gene. In some embodiments, removal of a sequence between two recombinase recognition sequences results in a decrease in the expression of a proximal transgene or a proximal homologous gene.

In some embodiments, the eukaryotic (e.g., mammalian, plant, yeast, nematode, parasite, or reptile) cell is present in vitro or ex vivo. In some embodiments, the eukaryotic (e.g., mammalian) cell is an epithelial cell, a lung cell, a kidney cell, an endothelial cell, a muscle cell, an adipose cell, a bone cell, a cartilage cell, or a neuron. In some embodiments, the eukaryotic (e.g., mammalian) cell is an undifferentiated cell or a stem cell (e.g., an embryonic stem cell). In some embodiments, the cell is implanted into a mammal following the contacting with the caged tamoxifen or caged tamoxifen derivative molecule and irradiation.

In some embodiments, the cell is present in a mammal (e.g., a mouse or rat). In some embodiments, the cell is present in the breast tissue, skin, kidney, lung, colon, liver, pancreas, stomach, intestine, colon, muscle, mammary gland, ovary, testes, prostate, brain, spinal cord, peripheral nerve, and heart. In some embodiments, the mammal is a child. In some embodiments, the mammal is an adult. In some embodiments, the mammal is a female. In some embodiments, the mammal is a male. In some embodiments, the mammal is an embryo or blastocyst.

In some embodiments, the composition is locally administered to a tissue containing the cell. In some embodiments, the composition is systemically administered (e.g., intravenous, intraarterial, intramuscular, intraperitoneal, subcutaneous, oral, transdermal, ocular, nasal, or intrathecal administration). In some embodiments, more than one dose of the composition is administered to the mammal before the cell is irradiated. In some embodiments, the composition is systemically administered and a specific target tissue is irradiated. In some embodiments, the composition is locally administered to a target tissue and the target tissue is irradiated.

In some embodiments, a mammal is administered a dose of between 1 mg to 500 mg of the composition (e.g., between 1 mg to 400 mg, between 1 mg to 300 mg, between 1 mg and 250 mg, between 1 mg and 200 mg, between 1 mg and 150 mg, between 1 mg and 100 mg, between 1 mg and 50 mg, between 5 mg and 50 mg, and between 5 mg and 40 mg).

In some embodiments, the cell is irradiated for a period of at least 1 minute (e.g., at least 5, 10, 15, 20, 30, 40, 50, or 60 minutes). In some embodiments, the cell is irradiated for a maximum of 15, 20, 25, 30, 35, 40, 45, 50, 55, or 60 minutes. In some embodiments, the cell is irradiated using any of the light sources described herein (e.g., a hand-held light source). In some embodiments, the cell is irradiated using an endoscopic or orthoscopic procedure. In some embodiments, the cell is irradiated using a two-photon light source. In some embodiments, the contacting and the irradiating occur within 24 hours of each other (e.g., within 20, 16, 12, 10, 8, 6, 4, 3, 2, or 1 hour of each other).

Methods of Treatment of Breast Cancer

Also provided are methods of treating a breast cancer in a mammal (e.g., human) that include administering a therapeutically effective amount of a composition containing a caged tamoxifen or a caged tamoxifen derivative (e.g., any of the caged tamoxifen or caged tamoxifen derivative molecules described herein), and irradiating a mammary tissue with light of between 200 nm to 900 nm (e.g., between 350 nm to 410 nm, between 200 nm and 700 nm, and between 700 nm and 900 nm), wherein the irradiating results in the release of tamoxifen or a tamoxifen derivative in the mammary tissue of the subject.

In some embodiments, the composition contains

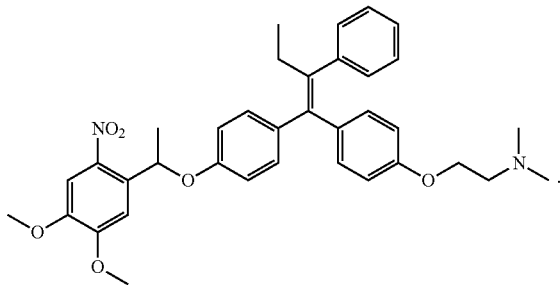

In some embodiments, the composition is formulated for sustained-release (e.g., formulated in a biodegradable polymer or a nanoparticle). In some embodiments, the composition is administered locally to the mammary tissue of the subject (e.g., local intraglandular, periglandular, subcutaneous, interductal, transdermal, or intramuscular administration). In some embodiments, the composition is administered systemically (e.g., oral, intravenous, intaarterial, intraperitoneal, intramuscular, or subcutaneous administration). In some embodiments, the composition is formulated for oral, intraglandular, periglandular, subcutaneous, interductal, intramuscular, intraperitoneal, intramuscular, intraarterial, transdermal, or intravenous administration).

In some embodiments, the subject is a female. In some embodiments, the subject is a male. In some embodiments, the subject is a child. In some embodiments, the subject is an adult (e.g., at least 18, 25, 30, 35, 40, 45, 50, 55, 60, 65, 70, 75, 80, 85, 90, 95, or 100 years old). In some embodiments, the subject has been diagnosed as having breast cancer. In some embodiments, the subject has been resistant to other breast cancer therapeutics.

A subject can be identified as having breast cancer by the detection or observation of one of more the following symptoms in a subject: breast lump or thickening, bloody discharge from a nipple, change in the size or shape of breast, changes to the skin over the breast, inverted nipple, peeling, flaking, or scaling of a nipple or breast skin, redness or pitting of the skin over the breast, mutations in the Her2/neu receptor, and mutations in BRCA1 or BRCA2. A subject can be diagnosed as having breast cancer by a medical professional (e.g., a physician, a nurse, a nurse's assistant, a physician's assistant, or a laboratory technician). The efficacy of a treatment of a breast cancer can be detected by a decrease in the size of a breast cancer tumor, a decrease in the spread of the breast cancer in the mammary tissue of the subject, a decrease in the rate of metastasis of breast cancer in the subject (e.g., as compared to a subject not receiving a treatment or receiving a different treatment for breast cancer), a decrease in the rate of growth of a breast cancer tumor in a subject, and a decrease in one or more physical symptoms of breast cancer (e.g., a decrease in one or more of the physical symptoms listed above).

In some embodiments, the subject is administered a dose of between 1 mg to 500 mg of any of the compositions described herein (e.g., between 1 mg to 400 mg, between 1 mg to 300 mg, between 1 mg and 250 mg, between 1 mg and 200 mg, between 1 mg and 150 mg, between 1 mg and 100 mg, between 1 mg and 50 mg, between 5 mg and 50 mg, and between 5 mg and 40 mg). The amount of the composition administered will depend on whether the composition is administered locally or systemically. A skilled artisan can further determine the appropriate dosage depending, for example, on the following factors: whether the administration is local or systemic, the age of the subject, the severity or stage of the disease, the other therapies administered to the subject, the subject's mass, the subject's sex, and the subject's responsiveness to other breast cancer therapeutics.

In some embodiments, the subject is administered more than one dose of the composition. In some embodiments, the subject is administered a dose of the composition at least once a month (e.g., at least twice a month, at least three times a month, at least four times a month, at least once a week, at least twice a week, three times a week, once a day, or twice a day). In some embodiments, the mammary tissue of the subject is irradiated within 24 hours (e.g., within 20, 16, 12, 10, 8, 6, 4, 2, or 1 hour) of the administration of the composition. In some embodiments, the mammary tissue of the subject is irradiated within 30 minutes (e.g., within 20 minutes, 15 minutes, 10 minutes, or 5 minutes) of the administration of the composition.

In some embodiments, the mammary tissue is irradiated for a period of at least 1 minute (e.g., at least 5, 10, 15, 20, 30, 40, 50, or 60 minutes). In some embodiments, the mammary tissue is irradiated for a maximum of 15, 20, 25, 30, 35, 40, 45, 50, 55, or 60 minutes. In some embodiments, the mammary tissue is irradiated using any of the light sources described herein (e.g., a hand-held light source). In some embodiments, the mammary tissue is irradiated using two-photon light source.

In some embodiments, serial rounds of contacting and irradiating can be performed in the subject (e.g., at least two rounds of contacting/irradiating). In some embodiments, the rounds of contacting/irradiating can be performed periodically (e.g., at least once a week, at least a month, at least once every two months, at least once every three months) in the subject over an extended period of time (e.g., a period of at least 2 weeks, at least one month, at least two months, at least six months, at least one year, and at least two years).

In some embodiments, the administering and irradiating are performed by a health care professional (e.g., a nurse, a nurse's assistant, a physician, a physician's assistant, or a laboratory technician). In some embodiments, the administering and irradiating are performed by the subject.

In some embodiments, the subject is administered one or more additional breast cancer therapeutics. In some embodiments, the one or more additional breast cancer therapeutics are selected from the group consisting of: cyclophosphamide, methotrexate, 5-fluorouracil, doxorubicin, paclitaxel, doxorubicin, epirubicin, trastuzumab, lapatinib, bevacizumab, abraxane, pamidronate, anastrozole, exemastane, fulvestrant, letrozole, gemcitabine, pegfilgrastim, filgrastin, doxetaxel, capecitabine, goserelin, zoledronic acid, and ixabepilone. In some embodiments, the compositions contain a caged tamoxifen or caged tamoxifen derivative molecule (e.g., any of the caged tamoxifen or caged tamoxifen derivative molecules described herein) and one or more additional breast cancer therapeutics (e.g., any of the additional breast cancer therapeutics described herein).

The invention is further described in the following example, which does not limit the scope of the invention described in the claims.

EXAMPLE

Example 1

Synthesis and Use of Caged 4-OHC to Achieve Precise Genetic Engineering Control in Mice In order to achieve cell-specific gene activation, a caged tamoxifen derivative molecule was synthesized and tested in a series of in vitro and in vivo photo activation experiments to determine whether it could reliably induce efficient light-dependent Cre-mediated recombination in mice. The methods and materials used in these experiments are described below.

Materials and Methods

Reagents and Instrument

Unless otherwise stated, all the reagents for the synthesis of caged 4-OHC were obtained from Sigma-Aldrich (St. Louis, Mo., USA) and used as received. $^1$H NMR spectra were recorded on a Varian 400 MHz spectrometer. High performance liquid chromatography-mass spectrometry (HPLC-MS) analysis was performed on a Waters (Milford, Mass.) LC-MS system. In the LC-MS system, electrospray ionization (ESI) was used to obtain mass spectrometry. A Waters XTerra C18 5-μm column was used for HPLC-MS analysis (eluents: 0.1% trifluoroacetic acid (v/v) in water and acetonitrile; gradient: 0-9.5 min, 5-100% B; 9.5-10.0 min 100% B). The chromatograms were processed using MassLynx software (from Waters). UV-Vis spectra were recorded in a TECAN microplate reader. A 6 W hand-held UV lamp (UVP, LLC) was used for uncaging the caged 4-OHC both in vitro and in vivo.

Mice

Homozygous Rosa26CreER$^{T2}$ (Ventura et al., *Nature* 445: 661-665, 2007), mT/mG (Muzumdar et al., *Genesis* 45:593-605, 2007), and R26R (Soriano et al., *Nat.* Genetics 21:70-71, 1999) mice in C57BL/6 background were obtained from The Jackson Laboratory (Stock Numbers: 8463, 7676 and 3474, respectively). Heterozygous Rosa26CreER$^{T2}$; mT/mG and Rosa26CreER$^{T2}$; R26R mice were generated by crossing the homozygous mice.

Synthesis of Caged 4-OHC

The DMNPE photoactivatable caging group and 4-OHC were synthesized as described (Sinha et al., *Chembiochem* 11:653-663, 2010; Dyer et al., *J. Org. Chem.* 64:7988-7995, 1999). DMNPE was conjugated to 4-OHC under Mitsonobu coupling conditions. Briefly, in a 25-mL round bottom flask, DMNPE (0.014 g, 0.063 mmol), 4-OHC (0.020 g, 0.057 mmol), and triphenyl phosphine (PPh$_3$, 0.016 g, 0.063 mmol) were mixed together in 0.5 mL of tetrahydrofuran (THF) under an argon atmosphere. After stirring the solution at room temperature (RT) for ~5 min, diisopropyl azodicarboxylate (DIAD, 0.012 ml, 0.063 mmol) was added dropwise to the reaction mixture. The reaction mixture was allowed to stir at RT for ~2.5 h. The crude product was directly charged to a SiO$_2$ column for purification (eluent: 100% dichloromethane to 10% methanol in dichloromethane v/v). Caged 4-OHC was isolated as a yellow solid. Yield=31%. $^1$H NMR (400 MHz, CDCl$_3$): 7.65 (s, 1H), 7.20 (s, 1H), 6.93 (m, 4H), 6.79 (d, $^2$J=8.8 Hz, 2H), 6.67 (d, $^2$J=8.8 Hz, 2H), 6.10 (q, $^4$J=6.13 Hz, 1H), 4.03 (t, $^3$J=5.8 Hz, 2H), 3.94 (s, 3H), 3.89 (s, 3H), 2.72 (t, $^3$J=5.8 Hz, 2H), 2.35 (s, 6H), 2.18 (m, 4H), 1.67 (d, $^2$J=6 Hz, 3H), 1.56 (m, 6H). MS (electrospray ionization mass spectrometry: ESI-MS) calculated: 560.29. found: 561.40 [M+H]$^+$.

UV-Vis and HPLC-MS Characterization of the Photocleavage of Caged 4-OHC

A 0.25 mM solution of caged 4-OHC in 1:1 (v/v) water: acetonitrile was used for the UV-Vis spectroscopic characterization of the photocleavage reaction. The solution of the caged 4-OHC was placed in a 96-well black clear bottom microplate. The solution was then irradiated at ~365 nm using a hand-held UV lamp. After light exposure, UV-Vis spectra of the solution was recorded in a TECAN microplate reader. A time course of the photocleavage reaction was monitored by exposing the caged 4-OHC solution to light for different durations, and subsequently recording the UV-Vis spectra of the solution.

A 2.0 mM solution of caged 4-OHC in 1:1 (v/v) water: acetonitrile was used for the HPLC-MS study. The solution of the caged 4-OHC was placed in a glass vial and irradiated at ~365 nm using a hand-held UV lamp. Aliquots were taken at different time intervals and injected to the HPLC-MS machine for analysis. Prism 5 (GraphPad, La Jolla, Calif.) for Mac was used to plot the data.

MEF Isolation and Photoactivation Procedure

Mouse embryonic fibroblasts (MEFs) were isolated as described (Sharpless et al., *Mol. Cell* 8:1187-1196, 2001) and grown in DMEM with 10% FBS. To shed UV light on the cells, the cells were first grown in 60-mm dish overnight to become nearly confluent. The next day, the medium was replaced with medium containing caged 4-OHC at 5 μM and incubated for 30 minutes. The cells were washed twice quickly with warm PBS and covered with fresh medium. The dish was placed on the UV emission surface of a handheld 6 W long-wavelength UV lamp (UVP, LLC), and UV light was kept on for a designated period of time. The cells were put back into the incubator to culture for 48-72 h before live imaging or flow cytometric analysis.

Mammary 3D Culture and Photoactivation Procedure.

Mouse mammary epithelial cells (MEFs) were isolated from 6-8 week old female Rosa26CreER$^{T2}$; mT/mG mice as previously described (Tiede et al., *PLoS One* 4:e8035, 2009). Briefly, mammary glands were excised, minced using scalpels, and digested for 1 hour in 300 U/mL type 1A collagenase (Sigma) and 100 U/mL hyaluronidase (Sigma). The cells were then treated with 0.25% trypsin/EDTA, dispase (Invitrogen)/DNase (Sigma), and ACK lysing buffer (Invitrogen) in succession. Between each treatment, cells were rinsed in MEGM (1:1 DMEM:F12 Ham supplemented with 5 mg/mL insulin, 500 ng/mL hydrocortisone, 10 ng/mL EGF, 20 ng/mL cholera toxin, 5% bovine calf serum, and 1× penicillin/streptomycin). Afterwards, cells were filtered twice through 40-mm nylon cell strainers and seeded in 35-mm dishes that contained a layer of Growth Factor Reduced Matrigel (BD Biosciences) measuring approximately 1-2 mm thickness. Acini usually formed in 4-8 days. During photoactivation, the acini were incubated with MEGM containing 5 μM caged 4-OHC for 1 hour. The cells were washed twice quickly with warm PBS and covered with fresh medium. The dish was placed on the UV emission surface of a hand-held 6 W long-wavelength UV lamp (UVP, LLC, exposure time: 1 minute) or above the 60× objective of an inverted epifluorescent microscope equipped with a standard DAPI filter set. The cells were returned to the incubator to culture for >48 h before live-cell imaging using an upright Zeiss 710 laser scanning confocal microscope equipped with 20× and 40× water immersion objectives.

Photoactivation Procedure in Mice

Female mice of 6-8 weeks old were clean shaven on the dorsal and ventral sides. The caged 4-OHC was dissolved in 20% Solutol for in vivo delivery. The vehicle or 1 mg caged 4-OHC in vehicle was injected intraperitoneally. One hour later, the mice were anesthetized with isoflurane and exposed to UV light from the hand-held 6 W long-wavelength UV lamp (UVP, LLC) for 15 minutes. Alternatively, for mammary tissue illumination, the right inguinal (#4) mammary fat pad was exposed by creating a small skin flap and illumination with UV light for 15 minutes. For enhanced photoconversion, this procedure was repeated four times. On the seventh day, the mice were imaged with Olympus OV-110 epifluorescence imager (Thurber et al., *PLoS One* 4:e8053, 2009) to detect fluorescent signals emitted from the skin on the dorsal and ventral sides. Alternatively, the left and right mammary glands were dissected and immediately imaged using the intravital laser scanning microscope IV-110 (Kelly et al., *PLoS Med.* 5:e85, 2008).

Results

A recently developed double-fluorescent Cre reporter mouse, the mT/mG strain (Muzumdar, *Genesis* 45:593, 2007) was used to design a biological system that can faithfully report on the induced activity of CreER. This mouse model expresses tdTomato prior to and EGFP following Cre-mediated recombination ubiquitously in tissues. The homozygous mT/mG mouse was crossed to the homozygous Rosa26CreER$^{T2}$ strain (Ventura et al., *Nature* 445:661, 2007), and the progeny, Rosa26CreER$^{T2}$; mT/mG, were heterozygous for both alleles. The photoinduced activity of caged tamoxifen and caged tamoxifen derivative molecules can be assessed by illuminating the cells and tissues from these mice and looking for EGFP-expressed cells (FIG. 1).

Figure 2:
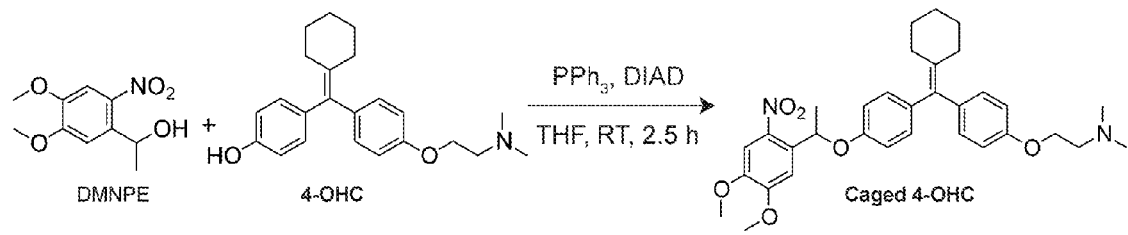
FIG. 2 is a schematic showing the synthesis of caged 4-OHC using Mitsonobu reaction conditions.
Figure 3:
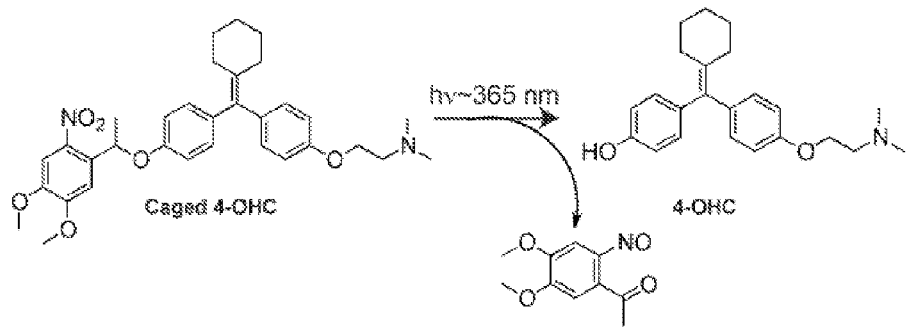
FIG. 3 is a schematic showing the photocleavage reaction of caged 4-OHC using 365 nm UV light.
Figure 4:
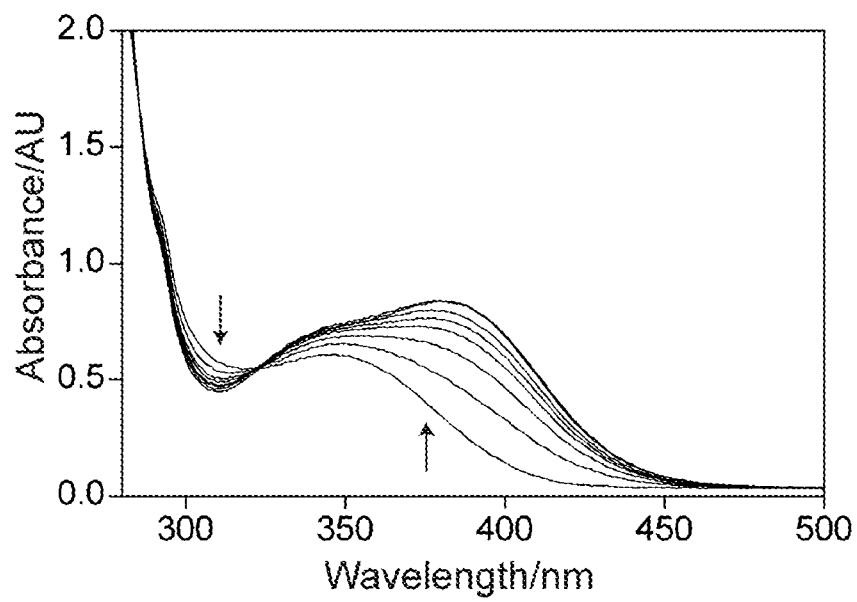
FIG. 4 is a set of absorbance spectra that show the changes in UV-Vis absorbance that occur during the photocleavage of caged 4-OHC in water:acetonitrile (1:1 v/v).
Figure 5:
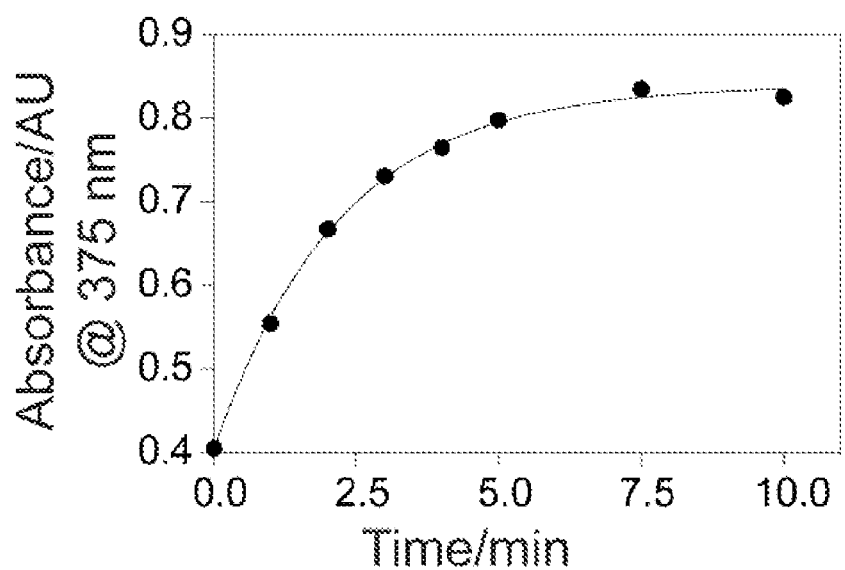
FIG. 5 is a graph showing the change in absorbance of caged 4-OHC at 375 nm over UV irradiation time.
Figure 6:
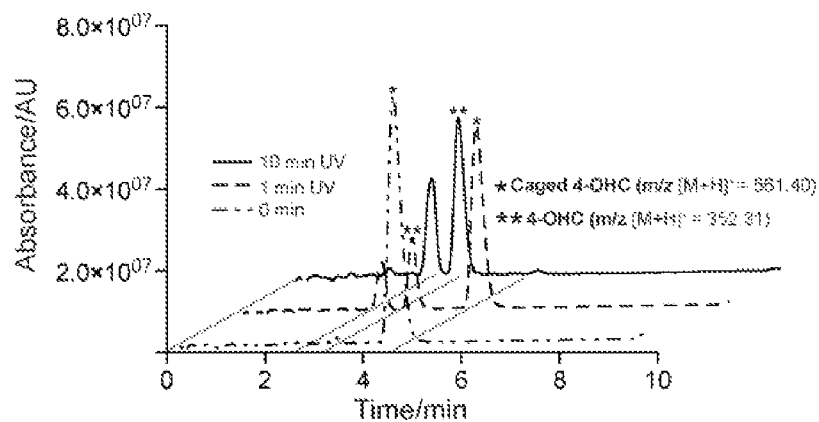
FIG. 6 is a set of three HPLC-MS chromatograms showing the quantitative release of 4-OHC from caged 4-OHC upon UV irradiation. The three chromatograms represent a UV exposure of 0 minute, 1 minute, and 10 minutes. The peaks corresponding to caged 4-OHC (*) and released 4-OHC (**) are indicated.

In these experiments, a 4-hydroxytamoxifen (4-OHT) analogue, 4-hydroxycyclofen (4-OHC), was used as a small molecule agonist of the ER component of the fusion protein. Although 4-OHT and 4-OHC have similar binding affinity to the ER, 4-OHC is preferred over 4-OHT in view of its synthetic accessibility and better photostability (Zinha et al., *Zebrafish* 7:199, 2010). As shown in FIG. 2, 4-OHC was caged by attaching a photolabile 1-(4,5-dimethoxy-2-nitrophenyl)ethyl (DMNPE) moiety to the free hydroxy group of 4-OHC using the Mitsonobu reaction (Zinha et al., *Zebrafish* 7:199, 2010). Under ambient light, the DMNPE caging group is stable in physiological conditions. However, exposure to long wavelength UV irradiation (~350-410 nm with a peak at 365 nm) leads to photolytic cleavage, releasing 4-OHC (FIG. 3). The photocleavage reaction of the caged 4-OHC was monitored by UV-Vis spectroscopy. A change in the UV-Vis absorption spectrum was observed when a solution of caged 4-OHC was exposed to a hand-held 365 nm UV lamp. This change was typical of the breakage of the DMNPE caging group (FIG. 4). The photochemical reaction was complete within 10 min of exposure (FIG. 5). High performance liquid chromatography-mass spectrometry (HPLC-MS) verified the chemical identity of the photoreleased products and also confirmed quantitative, unidirectional conversion to 4-OHC (FIG. 6). Overall, these characterizations indicate that the caged 4-OHC undergoes efficient photocleavage at 365 nm UV light and releases 4-OHC.

Figure 7:
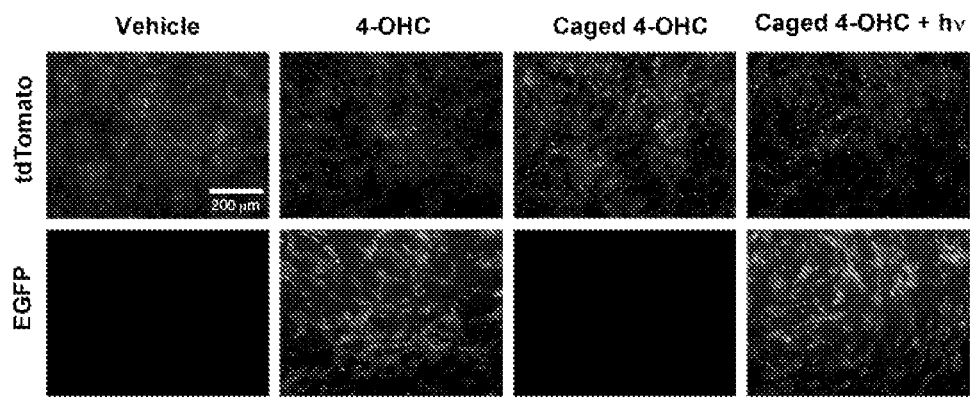
FIG. 7 is a set of eight fluorescent micrographs of mouse embryonic fibroblasts (MEFs) isolated from Rosa26CreER$^{T2}$; mT/mG mice following treatment with vehicle alone (two left panels), 4-OHC (two left center panels), caged 4-OHC (two right center panels), and caged 4-OHC with light exposure (two right panels).
Figure 8:
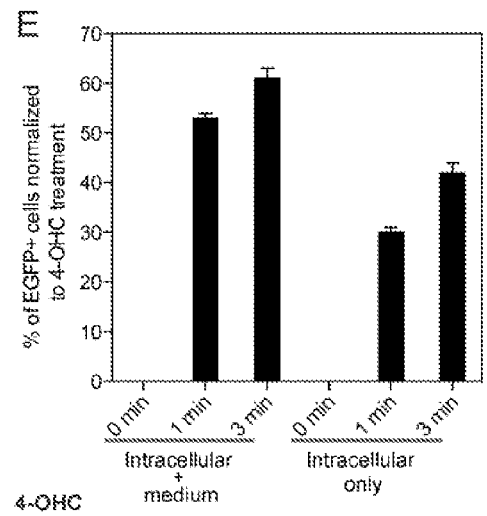
FIG. 8 is a graph showing the percentage of enhanced green fluorescent protein (EGFP)-positive MEFs (normalized to 4-OHC-treated MEF controls) in MEFs treated with 4-OHC or caged 4-OHC following different durations of UV activation. The "intracellular+medium" group represents cell samples without PBS wash before UV irradiation. The "intracellular only" group represents cell samples washed twice with PBS before UV irradiation.
Figure 9:
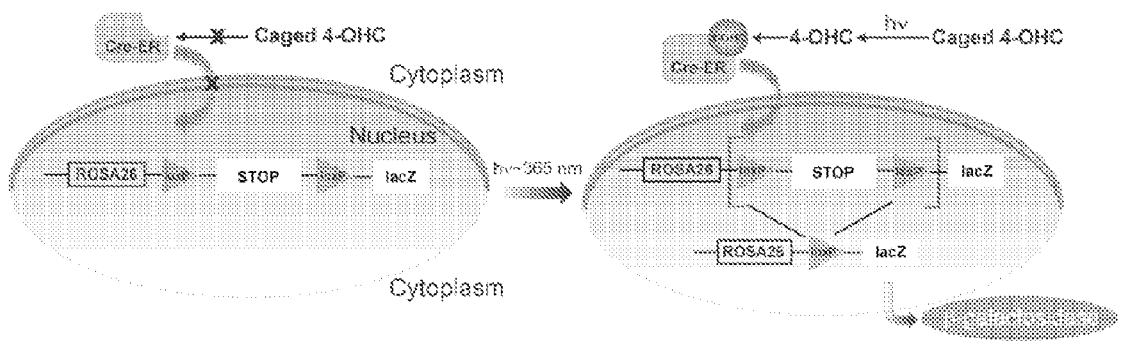
FIG. 9 is a schematic of the photoactivation-dependent CreER/loxP system in the Rosa26CreER$^{T2}$; R26R reporter mice. Photoactivated release of lacZ gene expression occurs in illuminated and caged 4-OHC-treated cells.
Figure 10:
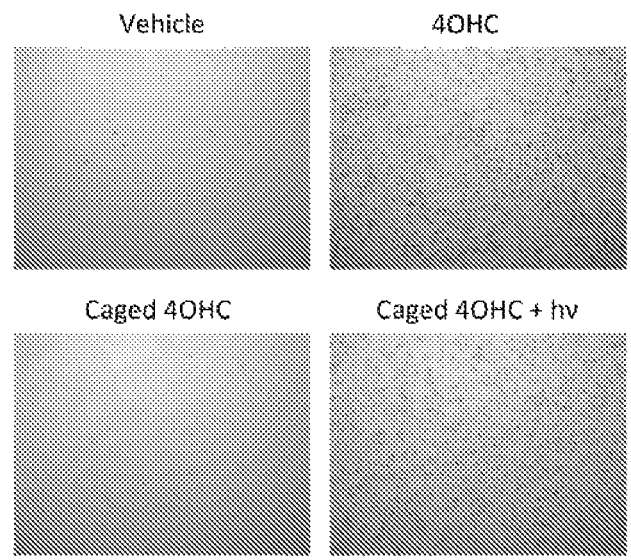
FIG. 10 is a set of four micrographs of X-gal stained MEFs from Rosa26CreER$^{T2}$; R26R mice embryos following treatment with vehicle alone (upper left panel), 4-OHC (upper right panel), caged 4-OHC (bottom left panel), and caged 4-OHC with 365 nm light exposure (bottom right panel).

Mouse embryonic fibroblasts (MEFs) isolated from the Rosa26CreER$^{T2}$; mT/mG mice in cell culture were used to test the caged 4-OHC activity. The Rosa26CreER$^{T2}$; mT/mG MEFs were treated with either 4-OHC or caged 4-OHC and illuminated at 365 nm. As expected, photocleavage of the caged 4-OHC induced EGFP expression in a stringent fashion (FIGS. 7 and 8). To further test the caged 4-OHC, another reporter mouse was generated (Rosa26CreER$^{T2}$; R26R mice). The Rosa26CreER$^{T2}$; R26R mice were generated by crossing homozygous Rosa26CreER$^{T2}$ mice with homozygous Rosa26-loxP-STOP-loxP-lacZ mice (experimental system shown in FIG. 9). Similar results were observed in the Rosa26CreER$^{T2}$; R26R MEFs (FIG. 10). No significant phototoxicity or cell viability changes due to the UV irradiation was observed in these experiments (energy density 1.6 mW/cm$^2$, photon energy 3.4 eV, number of photons per second per cm$^2$ 2×10$^{15}$, up to 3 min exposure time), consistent with other reports (Young et al., *Org. Biomol. Chem.* 5:999, 2007).

Figure 11:
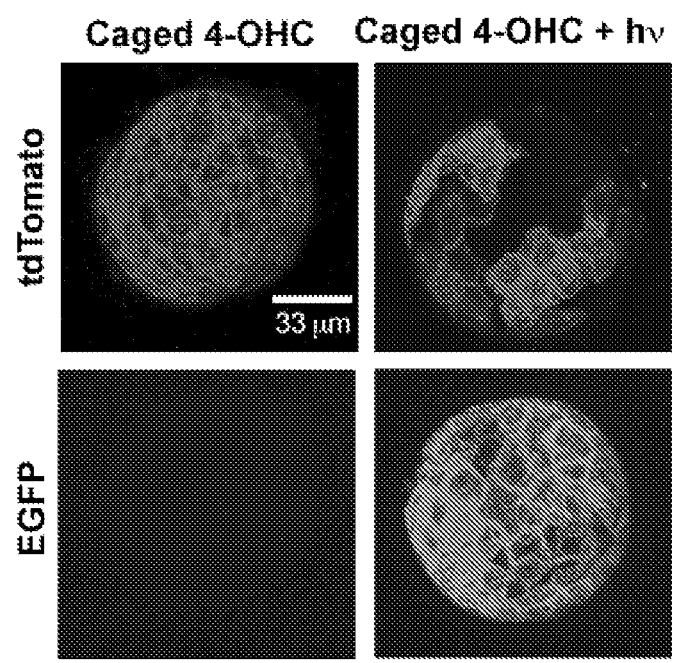
FIG. 11 is a set of four photomicrographs showing the EGFP expression induced by 365 nm UV activation of caged 4-OHC in mammary epithelial cells isolated from Rosa26CreER$^{T2}$; mT/mG female mice and cultured to form acini on Matrigel. The images shown are projections of the Z-stack confocal images.
Figure 12:
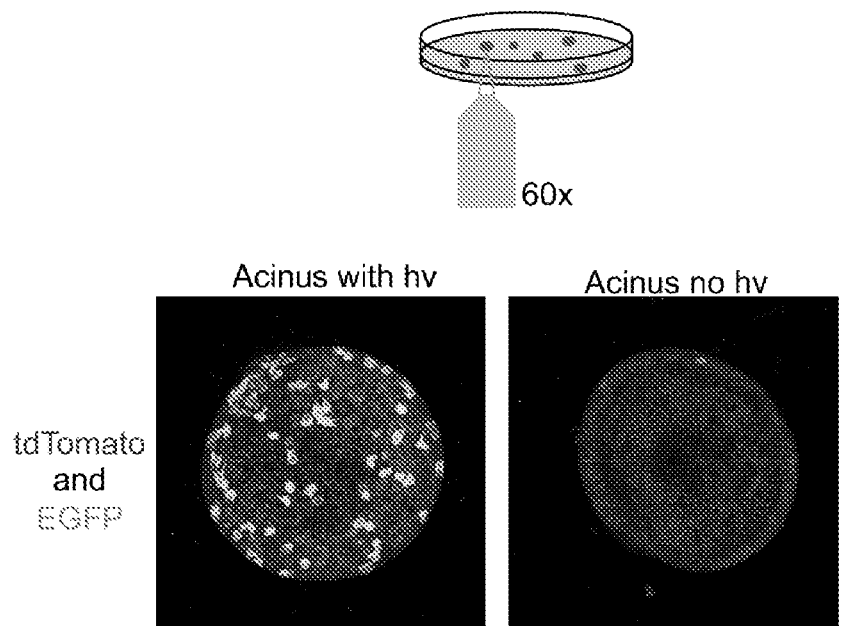
FIG. 12 is a graphic showing the culturing of mammary epithelial cell acini from Rosa26CreER$^{T2}$; mT/mG female mice and two fluorescent micrographs of individual acini. The acini were illuminated with the 60× objective of an inverted epifluorescent microscope equipped with a standard DAPI filter set for 1 minute after treatment with 5 µM caged 4-OHC and brief PBS wash. The fluorescent micrographs were collected four days later from the live acini using a laser scanning confocal microscope. The left panel is a micrograph of an acini treated with caged 4-OHC and exposed to light, and the right panel is a micrograph of an acini treated with caged 4-OHC and not exposed to light.

While a convenient system, 2D-cell culture cannot manifest all the biological responses of cells to external perturbations in a 3D-environment. Additional tests were performed in mammary acinus culture to determine whether caged 4-OHC would enable light-dependent Cre recombination in this well-established organoid model. Mammary epithelial cells from Rosa26CreER$^{T2}$; mT/mG mice were isolated and overlaid on a basement membrane to allow polarized acinar structure development. The formed acini were subjected to caged 4-OHC treatment with or without subsequent brief UV illumination by the UV lamp (energy density 1.6 mW/cm$^2$, photon energy 3.4 eV, number of photons per second per cm$^2$ 2×10$^{15}$, 1 min exposure time) (FIG. 11) or the 60× objective of an inverted fluorescent microscope equipped with a standard DAPI filter set (FIG. 12). Similar to the 2D-culture results, the caged 4-OHC allowed very tight control of EGFP expression in response to photoactivation in the mammary acini experimental model.

Figure 13:
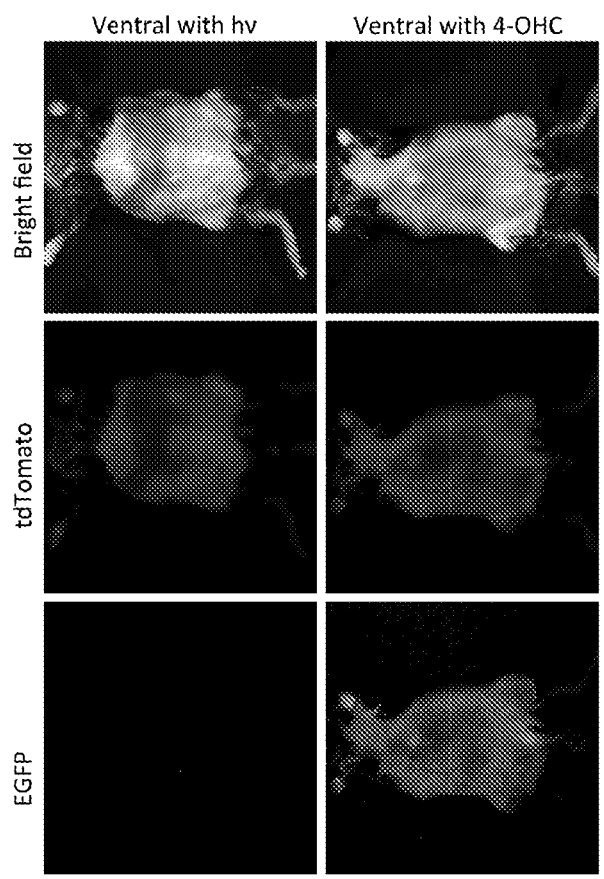
FIG. 13 is a set of six images showing the expression of EGFP in Rosa26CreER$^{T2}$; mT/mG mice following treatment with 4-OHC. EGFP expression was detected using an OV-110 epifluorescent imager. Mice treated with vehicle control and irradiated with 365 nm UV light are shown in the left panels. Mice treated with 4-OHC are shown in the right panels.
Figure 14:
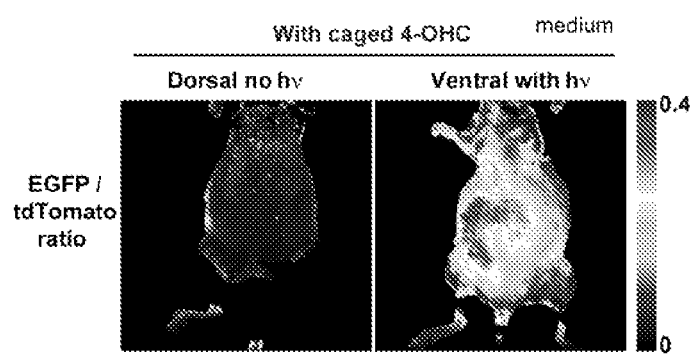
FIG. 14 is a set of two images showing the EGFP expression in the ventral skin of Rosa26CreER$^{T2}$; mT/mG reporter mice following treatment with caged 4-OHC and no light treatment (left panel) or caged 4-OHC with 365 nm light treatment. An increase in EGFP signal is followed by a decrease in tdTomato signal; low values of EGFP/tdTomato ratio correspond to low EGFP and high tdTomato, while high values of ratios correspond to high EGFP and low tdTomato.

Additional experiments were performed to determine whether caged 4-OHC is able to induce gene activation in vivo in mice upon photoactivation. These experiments focused on two organs: skin and mammary glands. A custom-built broad illumination method was used to perform this in vivo testing. In a first set of experiments, EGFP/tdTomato expression at the whole mouse level was assessed using the Olympus OV-110 epifluorescence imager. Very low green autofluorescence was detected in Rosa26CreER$^{T2}$; mT/mG mice when treated with vehicle control and irradiated with 365 nm UV, and strong EGFP signal was detected when treated with 4-OHC (FIG. 13). In a second experiment, Rosa26CreER$^{T2}$; mT/mG mice were injected intraperitoneally with caged 4-OHC and subjected to UV illumination only on the ventral (but not dorsal) skin. Resultant EGFP signal was observed on the ventral skin but not on the dorsal skin (FIG. 14) with an average 2.5-fold increase in fluorescence intensity. Because the increase of the EGFP signal was concomitant with the decrease of the tdTomato signal, EGFP/tdTomato ratios were also calculated in FIG. 14 for both ventral and dorsal skin.

Figure 15:
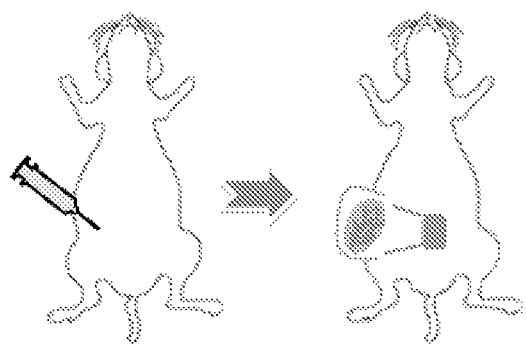
FIG. 15 is a schematic of the experimental design for intraperitoneal injection of vehicle or caged 4-OHC into the Rosa26CreER$^{T2}$; mT/mG female mice and subsequent 365 nm illumination on the right inguinal (#4) mammary fat pad.
Figure 16:
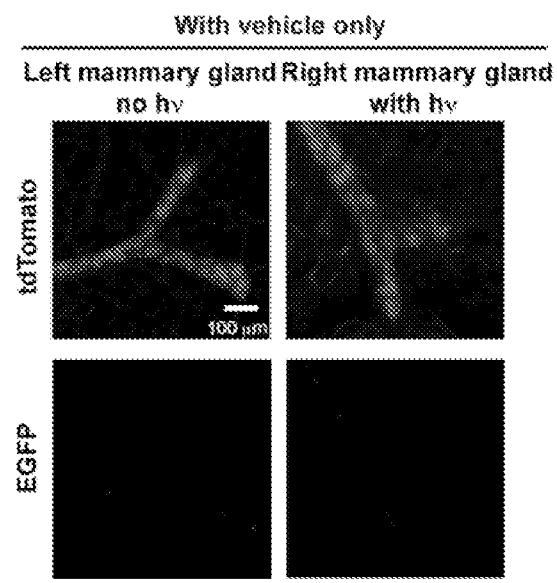
FIG. 16 is a set of four images of ex vivo mammary tissue from Rosa26CreER$^{T2}$; mT/mG female mice intraperitoneally injected with vehicle and exposed (right panels) or unexposed (left panels) to 365 nm light. The mammary tissue was imaged with an IV-110 epifluorescent imager.

A set of additional experiments was performed to determine whether caged 4-OHC could be used to induce CreER activity in the mammary glands of the female Rosa26CreER$^{T2}$; mT/mG mice following light exposure. The mice were injected with vehicle or caged 4-OHC, and only the right mammary gland was exposed to the 365 nm light, whereas the left was not (FIG. 15). Seven days later, the right and left mammary glands were resected for ex vivo imaging at a high spatial resolution using the Olympus Intravital Laser Scanning Microscope IV-110. The data show that 365 nm UV illumination of the mammary gland alone did not cause noticeable green autofluorescence increase or tissue morphological changes (FIG. 16). However, when caged 4-OHC was injected, the right, but not the left, mammary gland showed strong EGFP induction (FIG. 17). Taken together, the skin and mammary gland data clearly establish that the caged 4-OHC displayed superior in vivo inducibility by light and limited diffusion after uncaging to affect other organs.

Figure 18:
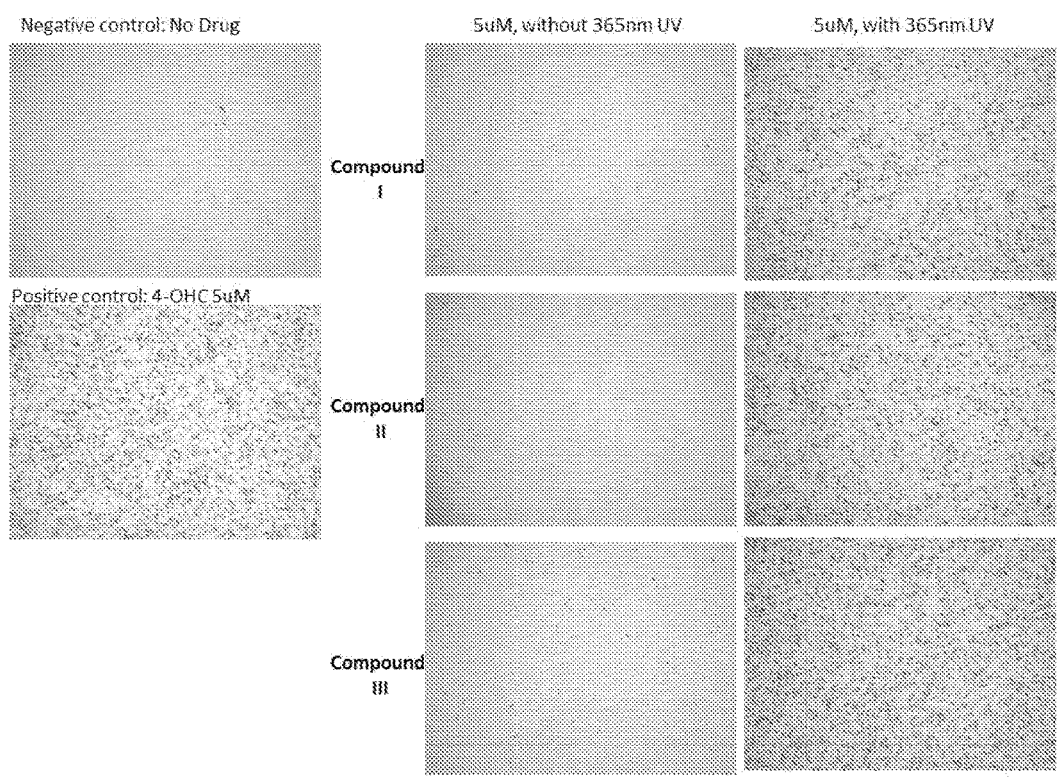
FIG. 18 is a set of eight photomicrographs showing the X-gal stained mouse embryonic fibroblasts from Rosa26-CreERT2; Lox-STOP-Lox-lacZ embryos following no treatment (upper left panel), treatment with 5 µM 4-OHC (positive control; lower left panel), treatment with Caged Molecule I ("Compound I") with or without 365 nm UV light exposure (top right and top center panels, respectively), treatment with Caged Molecule II ("Compound II") with or without 365 nm UV light exposure (middle right and middle center panels, respectively), or treatment with Caged Molecule III ("Compound III") with or without 365 UV light exposure (bottom right and bottom left panels, respectively).

An additional set of experiments were performed to test the ability of Caged Molecules I, II, and III (shown in Schematic #5) to induce nuclear translocation of a ER fusion protein in a cell following light exposure. Mouse embryonic fibroblasts from Rosa26-CreER$^{T2}$; Lox-STOP-Lox-lacZ embryos were treated with 5 µM 4-OHC (positive control; lower left panel), treat Caged Molecule I ("Compound I") with or without 365 nm UV light exposure (top right and top center panels, respectively), Caged Molecule II ("Compound II") with or without 365 nm UV light exposure (middle right and middle center panels, respectively), or Caged Molecule III ("Compound III") with or without 365 UV light exposure (bottom right and bottom left panels, respectively). The data show that irradiation of Caged Molecules I, II, and III resulted in an increase in the nuclear transport of the ER fusion protein (a CreER fusion protein) in the cells (FIG. 18).

In sum, the data show that the presently provided caged tamoxifen derivative molecules can efficiently regulate CreER-mediated recombination in a light-dependent manner in mice. One major advantage of using caged tamoxifen and caged tamoxifen derivative molecules over other methods of making Cre activity photo-regulatable is that one can seamlessly integrate the light into numerous existing CreER models to achieve an additional level of stringent control, i.e., regional- and cell-specific control of gene expression. For example, the villin-CreER$^{T2}$ mouse allows efficient target gene recombination throughout the entire digestive epithelium in response to systemic tamoxifen treatment (El Marjou et al., Genesis 39:186-193, 2004), and by restricting light activation of caged tamoxifen or caged tamoxifen derivative molecules to the colon, this mouse strain may become an excellent driver for spatiotemporal modeling of colorectal cancer in mice. Moreover, the application of this optochemogenetic (OCG) switch is not confined to CreER; as described further herein, it can provide photoregulation of a spectrum of ER-fusion proteins. These ER fusion proteins would be subject to tamoxifen- or tamoxifen derivative-dependent control of nuclear localization and protein activity in the nucleus. For example, such a fusion protein can be a telomerase-ER fusion protein (Jaskelioff et al., Nature 469:102-106, 2011). The OCG switch approach can use used in broad applications, especially in tumor and developmental biology, where localized and pattern-specific gene manipulation is of central importance to address many outstanding questions.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

The invention claimed is:
1. A composition comprising:

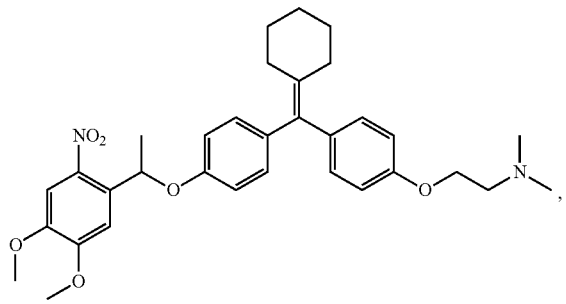 [SMILES: COc1cc(C(C)Oc2ccc(C(=C3CCCCC3)c3ccc(OCCN(C)C)cc3)cc2)c([N+](=O)[O-])cc1OC]

or a pharmaceutically acceptable salt thereof.

2. The composition of claim 1, wherein the composition contains at least 80% by weight of

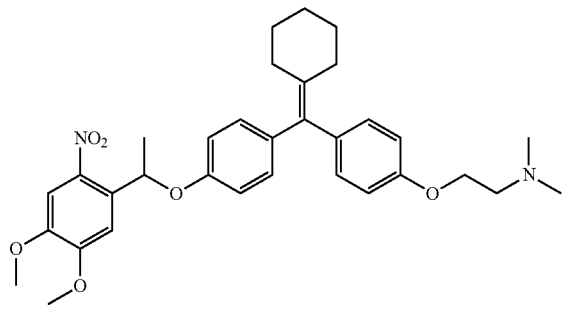 [SMILES: COc1cc(C(C)Oc2ccc(C(=C3CCCCC3)c3ccc(OCCN(C)C)cc3)cc2)c([N+](=O)[O-])cc1OC]

or a pharmaceutically acceptable salt thereof.

3. A kit comprising:
one or more doses of the composition of claim 1; and
a light source that emits light of a wavelength of between 350 nm to 410 nm.

4. A method of inducing nuclear translocation of a fusion protein comprising a human estrogen receptor ligand binding domain in a eukaryotic cell, the method comprising:
providing a eukaryotic cell that contains a fusion protein comprising a human estrogen receptor ligand binding domain,
contacting the eukaryotic cell with the composition of claim 1; and
irradiating the eukaryotic cell with a wavelength of light between 350 nm to 410 nm for a period of time sufficient to release 4-hydroxycyclofen from the composition,
wherein the released 4-hydroxycyclofen induces the nuclear translocation of the fusion protein.

5. The method of claim 4, wherein the eukaryotic cell is in a mammal.

6. The method of claim 5, wherein the eukaryotic cell is present in the mammary gland or the skin.

7. The method of claim 5, wherein the composition is locally administered to a target tissue in the mammal that contains the eukaryotic cell.

8. The method of claim 4, wherein the eukaryotic cell comprises a nucleic acid encoding the fusion protein, and the nucleic acid is stably integrated into a chromosome of the cell.

9. The method of claim 8, wherein the nucleic acid encoding the fusion protein is:
operably linked to a tissue-specific promoter sequence; or
operably linked to an inducible promoter sequence, and the eukaryotic cell is further contacted with a chemical inducing agent.

10. The method of claim 4, wherein the fusion protein comprises:
a sequence of a recombinase, and the fusion protein has recombinase enzymatic activity;
a sequence of a transcription factor, and the fusion protein is capable of promoting gene transcription in the nucleus of the eukaryotic cells;
a sequence of a transcription repressor, and the fusion protein is capable of repressing transcription of a gene in the nucleus of the eukaryotic cell;
a sequence of a histone deacetylase and the fusion protein has histone deacetylase activity;
a sequence of a histone acetyltransferase and the fusion protein has histone deacetylase activity;
a sequence of an O-6-methylguanosine-DNA methyltransferase and the fusion protein O-6-methylguanine-DNA methyltransferase activity;
a sequence of a telomerase, and the fusion protein has telomerase activity; or
a sequence of an oncogene.

11. The method of claim 4, wherein the eukaryotic cell is an undifferentiated cell, and the fusion protein comprises a sequence of a transcription factor or transcription repressor that induces cellular differentiation.

12. A method of inducing recombination in a eukaryotic cell, the method comprising:
providing a eukaryotic cell that comprises (i) a nucleic acid encoding a fusion protein comprising a sequence of a recombinase and a sequence of a human estrogen receptor ligand binding domain, wherein the fusion protein has recombinase activity, and (ii) a recombinase recognition sequence that is specifically recognized by the fusion protein, wherein both the nucleic acid encoding the fusion protein and the recombinase recognition sequence are integrated into a chromosome within the nucleus of the eukaryotic cell;
contacting the eukaryotic cell with a composition of claim 1; and
irradiating the eukaryotic cell with a wavelength of light between 350 nm to 410 nm for a period of time sufficient to release 4-hydroxycyclofen from the composition,
wherein the 4-hydroxycyclofen stimulates the nuclear importation of the fusion protein and the fusion protein stimulates recombination at the recombinase recognition sequence.

13. The method of claim 12, wherein the eukaryotic cell is in a mammal.

14. The method of claim 13, wherein the eukaryotic cell is present in the mammary gland or the skin.

15. The method of claim 13, wherein the composition is locally administered to a target tissue in the mammal that contains the eukaryotic cell.

16. The method claim 12, wherein the recombination results:
in a decrease in the expression of a transgene located between two recombinase recognition sequences in the chromosome;
in the replacement of a sequence between two recombinase recognition sequences with a new transgenic sequence; or in the increase in the proximity of a promoter or enhancer sequence to a transgene, wherein the recombination results in increased expression of the transgene.

17. The method of claim 12, wherein the nucleic acid encoding the fusion protein is:
   operably linked to tissue specific promoter sequence in the chromosome of the eukaryotic cell; or
   operably linked to an inducible promoter in the chromosome of the eukaryotic cell, and the eukaryotic cell is further contacted with a chemical inducing agent.

* * * * *

UNITED STATES PATENT AND TRADEMARK OFFICE
CERTIFICATE OF CORRECTION

PATENT NO. : 9,687,548 B2
APPLICATION NO. : 14/395210
DATED : June 27, 2017
INVENTOR(S) : Xin Lu et al.

Page 1 of 1

It is certified that error appears in the above-identified patent and that said Letters Patent is hereby corrected as shown below:

In the Claims

Column 64, Line 60:
In Claim 16, after "method" insert -- of --

Signed and Sealed this
Twenty-ninth Day of August, 2017

Joseph Matal
*Performing the Functions and Duties of the
Under Secretary of Commerce for Intellectual Property and
Director of the United States Patent and Trademark Office*